(12) United States Patent
Sabokbar et al.

(10) Patent No.: US 9,066,908 B2
(45) Date of Patent: Jun. 30, 2015

(54) METHOD OF TREATING BONE DISORDERS USING TSG-6

(75) Inventors: Afsie Sabokbar, Oxford (GB); Anthony Day, Manchester (GB); Caroline Milner, Manchester (GB)

(73) Assignee: University of Manchester, Manchester (GB)

( * ) Notice: Subject to any disclaimer, the term of this patent is extended or adjusted under 35 U.S.C. 154(b) by 727 days.

(21) Appl. No.: 12/281,920

(22) PCT Filed: Mar. 6, 2007

(86) PCT No.: PCT/GB2007/000772
§ 371 (c)(1),
(2), (4) Date: Oct. 31, 2008

(87) PCT Pub. No.: WO2007/101988
PCT Pub. Date: Sep. 13, 2007

(65) Prior Publication Data
US 2009/0099084 A1 Apr. 16, 2009

(30) Foreign Application Priority Data
Mar. 6, 2006 (GB) .................................. 0604460.6

(51) Int. Cl.
*A61K 38/00* (2006.01)
*A61K 38/17* (2006.01)
(52) U.S. Cl.
CPC ........... *A61K 38/1793* (2013.01); *A61K 38/177* (2013.01)

(58) Field of Classification Search
CPC .. A61K 38/00; A61K 38/1793; A61K 38/177
See application file for complete search history.

(56) References Cited

U.S. PATENT DOCUMENTS 5,194,596 A * 3/1993 Tischer et al. ................ 530/399
5,350,836 A * 9/1994 Kopchick et al. ............ 530/399
6,806,351 B2 * 10/2004 Ruben et al. ................. 530/350

FOREIGN PATENT DOCUMENTS

| EP | 0 705 842 | 4/1996 |
| WO | WO 92/12175 | 7/1992 |
| WO | WO 97/04075 | 2/1997 |
| WO | WO 02/081521 | 10/2002 |
| WO | WO 02081521 A2 * | 10/2002 |
| WO | WO 2005/060988 | 7/2005 |
| WO | WO 2005060988 A1 * | 7/2005 |

OTHER PUBLICATIONS

Roberts et al., (Eur Spine J. Feb. 2005;14(1):36-42. Epub Nov. 12, 2004).*
UniProt P98066 version 2 (Jun. 21, 2005).*
UniProt O00300, version 2 (May 27, 2002).*
Teitlebaum (Science. 2000;289:1504-1508).*
Chung-Faye et al., (Mol Med Today Feb. 2000 (6):82-87).*
Verma, et al., (Nature Sep. 18, 1987 389:239-242).*

(Continued)

*Primary Examiner* — Cherie M Stanfield
(74) *Attorney, Agent, or Firm* — Seed IP Law Group PLLC

(57) ABSTRACT

The invention provides use of a TSG-6 polypeptide, or a polynucleotide encoding an TSG-6 polypeptide, in the manufacture of a medicament for the treatment or prevention of a bone disease or condition associated with bone resorption by osteoclasts.

5 Claims, 5 Drawing Sheets

(56) References Cited

OTHER PUBLICATIONS

Juengst, (BMJ Jun. 28, 2003;326(7404):1410-1).*
Crystal (Science. Oct. 1995; 270:404-410).*
Tait et al., (Clin.Canc.Res., vol. 5, Jul. 1999, pp. 1708-1714).*
Benjamin et al., (Development.1998. 125:1591-1598).*
Vukicevic et al. (1996, PNAS USA 93:9021-9026).*
Massague, (Cell. 1987. 49:437-8).*
Pilbeam et al., (Bone. 1993. 14:717-720).*
Bárdos et al., "Anti-Inflammatory and Chondroprotective Effect of TSG-6 (Tumor Necrosis Factor-α-Stimulated Gene-6) in Murine Models of Experimental Arthritis," Am. J. Pathol. 159:1711-1721, 2001.
Bayliss et al., "Up-Regulation and Differential Expression of the Hyaluronan-Binding Protein TSG-6 in Cartilage and Synovium in Rheumatoid Arthritis and Osteoarthritis," Osteoarthritis Cartilage 9:42-48, 2001.
Blundell et al., "The Link Module from Ovulation - and Inflammation-associated Protein TSG-6 Changes Conformation on Hyaluronan Binding," J. Biol Chem. 278:49261-49270, 2003.
Day et al., "Overexpression, Purification, and Refolding of Link Module from Human TSG-6 in *Escherichia coli*: Effect of Temperature, Media, and Mutagenesis on Lysine Misincorporation at Arginine AGA Codons," Protein Expr. Purif. 8:1-16, 1996.
Getting et al., "The Link Module from Human TSG-6 Inhibits Neutrophil Migration in a Hyaluronan - and Inter-α-Inhibitor-Independent Manner," J. Biol. Chem. 277:51068-51076, 2002.
Glant et al., "Cartilage-Specific Constitutive Expression of TSG-6 Protein (Product of Tumor Necrosis Factor α-Stimulated Gene 6) Provides a Chondroprotective, but not Antiinflammatory, Effect in Antigen-Induced Arthritis," Arthritis Rheum. 46:2207-2218, 2002.
Ikeda et al., "The Promyelotic Leukemia Zinc Finger Promotes Osteoblastic Differentiation of Human Mesenchymal Stem Cells as an Upstream Regulator of CBFA1," J. Biol. Chem. 280:8523-8530, 2005.
Inoue et al., "Current Topics in Pharmacological Research on Bone Metabolism: Promyelotic Leukemia Zinc Finger (PLZF) and Tumor Necrosis Factor-α-Stimulated Gene 6 (TSG-6) Identified by Gene Expression Analysis Play Roles in the Pathogenesis of Ossification of the Posterior Longitudinal Ligament," J. Pharmacol. Sci. 100:205-210, 2006.
Kuznetsova et al. "The N-terminal Module of Thrombospondin-1 Interacts with the Link Domain of TSG-6 and Enhances its Covalent Association with the Heavy Chains of Inter-α-Trypsin Inhibitor," J. Biol. Chem. 280:30899-30908, 2005.
Mahoney et al., "Mapping the Hyaluronan-binding Site on the Link Module from Human Tumor Necrosis Factor-stimulated Gene-6 by Site-directed Mutagenesis," J. Biol. Chem. 276:22764-22771, 2001.
Mahoney et al., "Characterization of the Interaction Between Tumor Necrosis Factor-Stimulated Gene-6 and Heparin: Implications for the Inhibition of Plasmin in Extracellular Matrix Microenvironments," J. Biol. Chem. 280:27044-27055, 2005.
Maier et al., "TSG-6 Expression in Human Articular Chondrocytes. Possible Implications in Joint Inflammation and Cartilage Degradation," Arthritis Rheum. 39:552-559, 1996.
Margerie et al., "Complexity of IL-1β Induced Gene Expression Pattern in Human Articular Chondrocytes," Osteoarthritis Cartilage 5:129-138, 1997.
Marshall et al., "Blood-Based Biomarkers for Detecting Mild Osteoarthritis in the Human Knee," Osteoarthritis Cartilage 13:861-871, 2005.
Milner et al., "TSG-6: A Multifunctional Protein Associated with Inflammation," J. Cell Sci. 116:1863-1873, 2003.
Milner et al., "TSG-6: A Pluripotent Inflammatory Mediator?" Biochem. Soc. Trans. 34:446-450, 2006.
Mindrescu et al., "Amelioration of Collagen-Induced Arthritis in DBA/1J Mice by Recombinant TSG-6, a Tumor Necrosis Factor/ Interleukin-1-Inducible Protein," Arthritis Rheum. 43:2668-2677, 2000.
Mindrescu et al., "Reduced Susceptibility to Collagen-Induced Arthritis in DBA/1J Mice Expressing the TSG-6 Transgene," Arthritis Rheum. 46:2453-2464, 2002.
Nentwich et al., "A Novel Allelic Variant of the Human *TSG-6* Gene Encoding an Amino Acid Difference in the CUB Module. Chromosomal Localization, Frequency Analysis, Modeling, and Expression," J. Biol. Chem. 277:15354-15362, 2002.
Parkar et al., "Overlapping Sites on the Link Module of Human TSG-6 Mediate Binding to Hyaluronan and Chondroitin-4-Sulphate," FEBS Lett. 410:413-417, 1997.
Parkar et al., "TSG-6 Interacts with Hyaluronan and Aggrecan in a pH-Dependent Manner Via a Common Functional Element: Implications for its Regulation in Inflamed Cartilage," FEBS Lett. 428:171-176, 1998.
Rugg et al., "Characterization of Complexes Formed Between TSG-6 and iInter-α-Inhibitor that Act as Intermediates in the Covalent Transfer of Heavy Chains onto Hyaluronan," J. Biol. Chem. 280:25674-25686, 2005.
Salustri et al., "PTX3 Plays a Key Role in the Organization of the Cumulus Oophorus Extracellular Matrix and in In Vivo Fertilization," Development 131:1577-1586, 2004.
Stöve et al., "Interleukin-1β Induces Different Gene Expression of Stromelysin, Aggrecan and Tumor-Necrosis-Factor-Stimulated Gene 6 in Human Osteoarthritic Chondrocytes in vitro," Pathobiology 68:144-149, 2000.
Szántóet al., "Enhanced Neutrophil Extravasation and Rapid Progression of Proteoglycan-Induced Arthritis in TSG-6-Knockout Mice," Arthritis Rheum. 50:3012-3022, 2004.
Tsukahara et al., "Tumour Necrosis Factor α-Stimulated Gene-6 Inhibits Osteoblastic Differentiation of Human Mesenchymal Stem Cells Induced by Osteogenic Differentiation Medium and BMP-2," Biochem. J. 398:595-603, 2006.
Valdes et al., "Association Study of Candidate Genes for the Prevalence and Progression of Knee Osteoarthritis," Arthritis Rheum. 50:2497-2507, 2004.
Wisniewski et al., "TSG-6: a TNF-, IL-1-, and LPS-Inducible Secreted Glycoprotein Associated with Arthritis," J. Immunol. 151:6593-6601, 1993.
Wisniewski et al., "TNF/IL-1-inducible Protein TSG-6 Potentiates Plasmin Inhibition by Inter-α-inhibitor and Exerts a Strong Anti-inflammatory Effect In Vivo," J. Immunol. 156:1609-1615, 1996.
International Search Report for International Application No. PCT/GB2007/000772, dated Mar. 6, 2007.
International Preliminary Report on Patentability for International Application No. PCT/GB2007/000772, dated Mar. 6, 2007.
Kostenuik, "Osteoprotegerin and RANKL Regulate Bone Resorption, Density, Geometry and Strength," Curr. Opin. Pharmacol. 5:618-625, 2005.
Kong et al., "Activated T Cells Regulate Bone Loss and Joint Destruction in Adjuvant Arthritis Through Osteoprotegerin Ligand," Nature 402:304-309, 1999.

* cited by examiner

SEQUENCE LISTING

```
<160> NUMBER OF SEQ ID NOS: 15

<210> SEQ ID NO 1
<211> LENGTH: 1440
<212> TYPE: DNA
<213> ORGANISM: Homo sapiens
<220> FEATURE:
<221> NAME/KEY: CDS
<222> LOCATION: (77)..(910)

<400> SEQUENCE: 1
cagtcacatt tcagccactg ctctgagaat ttgtgagcag cccctaacag gctgttactt      60
cactacaact gacgat atg atc atc tta att tac tta ttt ctc ttg cta tgg    112
               Met Ile Ile Leu Ile Tyr Leu Phe Leu Leu Leu Trp
                 1               5                  10 gaa gac act caa gga tgg gga ttc aag gat gga att ttt cat aac tcc     160
Glu Asp Thr Gln Gly Trp Gly Phe Lys Asp Gly Ile Phe His Asn Ser
         15                  20                  25 ata tgg ctt gaa cga gca gcc ggt gtg tac cac aga gaa gca cgg tct     208
Ile Trp Leu Glu Arg Ala Ala Gly Val Tyr His Arg Glu Ala Arg Ser
 30                  35                  40 ggc aaa tac aag ctc acc tac gca gaa gct aag gcg gtg tgt gaa ttt     256
Gly Lys Tyr Lys Leu Thr Tyr Ala Glu Ala Lys Ala Val Cys Glu Phe
45                  50                  55                  60 gaa ggc ggc cat ctc gca act tac aag cag cta gag gca gcc aga aaa     304
Glu Gly Gly His Leu Ala Thr Tyr Lys Gln Leu Glu Ala Ala Arg Lys
                 65                  70                  75 att gga ttt cat gtc tgt gct gct gga tgg atg gct aag ggc aga gtt     352
Ile Gly Phe His Val Cys Ala Ala Gly Trp Met Ala Lys Gly Arg Val
             80                  85                  90 gga tac ccc att gtg aag cca ggg ccc aac tgt gga ttt gga aaa act     400
Gly Tyr Pro Ile Val Lys Pro Gly Pro Asn Cys Gly Phe Gly Lys Thr
         95                 100                 105 ggc att att gat tat gga atc cgt ctc aat agg agt gaa aga tgg gat     448
Gly Ile Ile Asp Tyr Gly Ile Arg Leu Asn Arg Ser Glu Arg Trp Asp
110                 115                 120 gcc tat tgc tac aac cca cac gca aag gag tgt ggt ggc gtc ttt aca     496
Ala Tyr Cys Tyr Asn Pro His Ala Lys Glu Cys Gly Gly Val Phe Thr
125                 130                 135                 140 gat cca aag caa att ttt aaa tct cca ggc ttc cca aat gag tac gaa     544
Asp Pro Lys Gln Ile Phe Lys Ser Pro Gly Phe Pro Asn Glu Tyr Glu
                145                 150                 155 gat aac caa atc tgc tac tgg cac att aga ctc aag tat ggt cag cgt     592
Asp Asn Gln Ile Cys Tyr Trp His Ile Arg Leu Lys Tyr Gly Gln Arg
            160                 165                 170 att cac ctg agt ttt tta gat ttt gac ctt gaa gat gac cca ggt tgc     640
Ile His Leu Ser Phe Leu Asp Phe Asp Leu Glu Asp Asp Pro Gly Cys
        175                 180                 185 ttg gct gat tat gtt gaa ata tat gac agt tac gat gat gtc cat ggc     688
Leu Ala Asp Tyr Val Glu Ile Tyr Asp Ser Tyr Asp Asp Val His Gly
        190                 195                 200 ttt gtg gga aga tac tgt gga gat gag ctt cca gat gac atc atc agt     736
Phe Val Gly Arg Tyr Cys Gly Asp Glu Leu Pro Asp Asp Ile Ile Ser
205                 210                 215                 220
```

```
aca gga aat gtc atg acc ttg aag ttt cta agt gat gct tca gtg aca      784
Thr Gly Asn Val Met Thr Leu Lys Phe Leu Ser Asp Ala Ser Val Thr
            225                 230                 235 gct gga ggt ttc caa atc aaa tat gtt gca atg gat cct gta tcc aaa      832
Ala Gly Gly Phe Gln Ile Lys Tyr Val Ala Met Asp Pro Val Ser Lys
            240                 245                 250 tcc agt caa gga aaa aat aca agt act act tct act gga aat aaa aac      880
Ser Ser Gln Gly Lys Asn Thr Ser Thr Thr Ser Thr Gly Asn Lys Asn
            255                 260                 265 ttt tta gct gga aga ttt agc cac tta taa aaaaaaaaaa aaggatgatc        930
Phe Leu Ala Gly Arg Phe Ser His Leu
            270                 275 aaaacacaca gtgtttatgt tggaatcttt tggaactcct ttgatctcac tgttattatt   990
aacatttatt tattattttt ctaaatgtga aagcaataca taatttaggg aaaattggaa   1050
aatataggaa actttaaacg agaaaatgaa acctctcata atcccactgc atagaaataa   1110
caagcgttaa cattttcata ttttttctt tcagtcattt ttctatttgt ggtatatgta    1170
tatatgtacc tatatgtatt tgcatttgaa attttggaat cctgctctat gtacagtttt   1230
gtattatact ttttaaatct tgaactttat aaacattttc tgaaatcatt gattattcta   1290
caaaaacatg attttaaaca gctgtaaaat attctatgat atgaatgttt tatgcattat   1350
ttaagcctgt ctctattgtt ggaatttcag gtcattttca taaatattgt tgcaataaat   1410
atccttgaac acaaaaaaaa aaaaaaaaaa                                    1440

<210> SEQ ID NO 2
<211> LENGTH: 277
<212> TYPE: PRT
<213> ORGANISM: Homo sapiens

<400> SEQUENCE: 2

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190
```

```
Val Glu Ile Tyr Asp Ser Tyr Asp Val His Gly Phe Val Gly Arg
        195                 200                 205

Tyr Cys Gly Asp Glu Leu Pro Asp Asp Ile Ile Ser Thr Gly Asn Val
210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
            275

<210> SEQ ID NO 3
<211> LENGTH: 260
<212> TYPE: PRT
<213> ORGANISM: Homo sapiens

<400> SEQUENCE: 3

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
                20                  25                  30

Thr Tyr Ala Glu Ala Lys Ala Val Cys Glu Phe Glu Gly Gly His Leu
            35                  40                  45

Ala Thr Tyr Lys Gln Leu Glu Ala Ala Arg Lys Ile Gly Phe His Val
        50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
                100                 105                 110

Pro His Ala Lys Glu Cys Gly Gly Val Phe Thr Asp Pro Lys Gln Ile
            115                 120                 125

Phe Lys Ser Pro Gly Phe Pro Asn Glu Tyr Glu Asp Asn Gln Ile Cys
        130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175

Glu Ile Tyr Asp Ser Tyr Asp Asp Val His Gly Phe Val Gly Arg Tyr
                180                 185                 190

Cys Gly Asp Glu Leu Pro Asp Asp Ile Ile Ser Thr Gly Asn Val Met
            195                 200                 205

Thr Leu Lys Phe Leu Ser Asp Ala Ser Val Thr Ala Gly Gly Phe Gln
        210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
        260

<210> SEQ ID NO 4
```

<211> LENGTH: 1440
<212> TYPE: DNA
<213> ORGANISM: Homo sapiens
<220> FEATURE:
<221> NAME/KEY: CDS
<222> LOCATION: (77)..(910)

<400> SEQUENCE: 4

```
cagtcacatt tcagccactg ctctgagaat ttgtgagcag cccctaacag gctgttactt        60
cactacaact gacgat atg atc atc tta att tac tta ttt ctc ttg cta tgg       112
                  Met Ile Ile Leu Ile Tyr Leu Phe Leu Leu Leu Trp
                   1               5                  10 gaa gac act caa gga tgg gga ttc aag gat gga att ttt cat aac tcc          160
Glu Asp Thr Gln Gly Trp Gly Phe Lys Asp Gly Ile Phe His Asn Ser
                15                  20                  25 ata tgg ctt gaa cga gca gcc ggt gtg tac cac aga gaa gca cgg tct          208
Ile Trp Leu Glu Arg Ala Ala Gly Val Tyr His Arg Glu Ala Arg Ser
 30                  35                  40 ggc aaa tac aag ctc acc tac gca gaa gct aag gcg gtg tgt gaa ttt          256
Gly Lys Tyr Lys Leu Thr Tyr Ala Glu Ala Lys Ala Val Cys Glu Phe
 45                  50                  55                  60 gaa ggc ggc cat ctc gca act tac aag cag cta gag gca gcc aga aaa          304
Glu Gly Gly His Leu Ala Thr Tyr Lys Gln Leu Glu Ala Ala Arg Lys
                 65                  70                  75 att gga ttt cat gtc tgt gct gct gga tgg atg gct aag ggc aga gtt          352
Ile Gly Phe His Val Cys Ala Ala Gly Trp Met Ala Lys Gly Arg Val
                 80                  85                  90 gga tac ccc att gtg aag cca ggg ccc aac tgt gga ttt gga aaa act          400
Gly Tyr Pro Ile Val Lys Pro Gly Pro Asn Cys Gly Phe Gly Lys Thr
                 95                 100                 105 ggc att att gat tat gga atc cgt ctc aat agg agt gaa aga tgg gat          448
Gly Ile Ile Asp Tyr Gly Ile Arg Leu Asn Arg Ser Glu Arg Trp Asp
                110                 115                 120 gcc tat tgc tac aac cca cac gca aag gag tgt ggt ggc gtc ttt aca          496
Ala Tyr Cys Tyr Asn Pro His Ala Lys Glu Cys Gly Gly Val Phe Thr
125                 130                 135                 140 gat cca aag cgg att ttt aaa tct cca ggc ttc cca aat gag tac gaa          544
Asp Pro Lys Arg Ile Phe Lys Ser Pro Gly Phe Pro Asn Glu Tyr Glu
                145                 150                 155 gat aac caa atc tgc tac tgg cac att aga ctc aag tat ggt cag cgt          592
Asp Asn Gln Ile Cys Tyr Trp His Ile Arg Leu Lys Tyr Gly Gln Arg
            160                 165                 170 att cac ctg agt ttt tta gat ttt gac ctt gaa gat gac cca ggt tgc          640
Ile His Leu Ser Phe Leu Asp Phe Asp Leu Glu Asp Asp Pro Gly Cys
                175                 180                 185 ttg gct gat tat gtt gaa ata tat gac agt tac gat gat gtc cat ggc          688
Leu Ala Asp Tyr Val Glu Ile Tyr Asp Ser Tyr Asp Asp Val His Gly
                190                 195                 200 ttt gtg gga aga tac tgt gga gat gag ctt cca gat gac atc atc agt          736
Phe Val Gly Arg Tyr Cys Gly Asp Glu Leu Pro Asp Asp Ile Ile Ser
205                 210                 215                 220 aca gga aat gtc atg acc ttg aag ttt cta agt gat gct tca gtg aca          784
Thr Gly Asn Val Met Thr Leu Lys Phe Leu Ser Asp Ala Ser Val Thr
                225                 230                 235 gct gga ggt ttc caa atc aaa tat gtt gca atg gat cct gta tcc aaa          832
Ala Gly Gly Phe Gln Ile Lys Tyr Val Ala Met Asp Pro Val Ser Lys
                240                 245                 250 tcc agt caa gga aaa aat aca agt act act tct act gga aat aaa aac          880
Ser Ser Gln Gly Lys Asn Thr Ser Thr Thr Ser Thr Gly Asn Lys Asn
                255                 260                 265
```

```
ttt tta gct gga aga ttt agc cac tta taa aaaaaaaaaa aaggatgatc    930
Phe Leu Ala Gly Arg Phe Ser His Leu
    270                 275 aaaacacaca gtgtttatgt tggaatctttt tggaactcct ttgatctcac tgttattatt    990
aacatttatt tattattttt ctaaatgtga aagcaataca taatttaggg aaaattggaa   1050
aatataggaa actttaaacg agaaaatgaa acctctcata atcccactgc atagaaataa   1110
caagcgttaa cattttcata ttttttttctt tcagtcattt ttctatttgt ggtatatgta   1170
tatatgtacc tatatgtatt tgcatttgaa attttggaat cctgctctat gtacagtttt   1230
gtattatact ttttaaatct tgaactttat aaacattttc tgaaatcatt gattattcta   1290
caaaaacatg attttaaaca gctgtaaaat attctatgat atgaatgttt tatgcattat   1350
ttaagcctgt ctctattgtt ggaatttcag gtcattttca taaatattgt tgcaataaat   1410
atccttgaac acaaaaaaaa aaaaaaaaaa   1440

<210> SEQ ID NO 5
<211> LENGTH: 277
<212> TYPE: PRT
<213> ORGANISM: Homo sapiens

<400> SEQUENCE: 5

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly His
        50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
```

```
                   260                 265                 270

Arg Phe Ser His Leu
            275

<210> SEQ ID NO 6
<211> LENGTH: 260
<212> TYPE: PRT
<213> ORGANISM: Homo sapiens

<400> SEQUENCE: 6

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Phe Glu Gly Gly His Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 7
<211> LENGTH: 93
<212> TYPE: PRT
<213> ORGANISM: Homo sapiens

<400> SEQUENCE: 7

Val Tyr His Arg Glu Ala Arg Ser Gly Lys Tyr Lys Leu Thr Tyr Ala
1               5                   10                  15

Glu Ala Lys Ala Val Cys Glu Phe Glu Gly Gly His Leu Ala Thr Tyr
            20                  25                  30

Lys Gln Leu Glu Ala Ala Arg Lys Ile Gly Phe His Val Cys Ala Ala
```

```
                    35                  40                  45
Gly Trp Met Ala Lys Gly Arg Val Gly Tyr Pro Ile Val Lys Pro Gly
                50                  55                  60
Pro Asn Cys Gly Phe Gly Lys Thr Gly Ile Ile Asp Tyr Gly Ile Arg
 65                 70                  75                  80
Leu Asn Arg Ser Glu Arg Trp Asp Ala Tyr Cys Tyr Asn
                85                  90

<210> SEQ ID NO 8
<211> LENGTH: 319
<212> TYPE: DNA
<213> ORGANISM: Artificial sequence
<220> FEATURE:
<223> OTHER INFORMATION: Link_TSG-6
<220> FEATURE:
<221> NAME/KEY: CDS
<222> LOCATION: (14)..(313)

<400> SEQUENCE: 8
aggagatata cat atg ggt gtg tac cac cgt gaa gca cgg tct ggc aaa       49
            Met Gly Val Tyr His Arg Glu Ala Arg Ser Gly Lys
             1               5                  10 tac aag ctc acc tac gca gaa gct aag gcg gtg tgt gaa ttt gaa ggc      97
Tyr Lys Leu Thr Tyr Ala Glu Ala Lys Ala Val Cys Glu Phe Glu Gly
             15                  20                  25 ggc cat ctc gca act tac aag cag cta gag gca gcc cgt aaa att gga     145
Gly His Leu Ala Thr Tyr Lys Gln Leu Glu Ala Ala Arg Lys Ile Gly
         30                  35                  40 ttt cat gtc tgt gct gct gga tgg atg gct aag ggc cgt gtt gga tac     193
Phe His Val Cys Ala Ala Gly Trp Met Ala Lys Gly Arg Val Gly Tyr
 45                  50                  55                  60 ccc att gtg aag cca ggg ccc aac tgt gga ttt gga aaa act ggc att     241
Pro Ile Val Lys Pro Gly Pro Asn Cys Gly Phe Gly Lys Thr Gly Ile
                 65                  70                  75 att gat tat gga atc cgt ctc aat agg agt gaa cgt tgg gat gcc tat     289
Ile Asp Tyr Gly Ile Arg Leu Asn Arg Ser Glu Arg Trp Asp Ala Tyr
             80                  85                  90 tgc tac aac cca cac gca aag taa gaattc                              319
Cys Tyr Asn Pro His Ala Lys
         95

<210> SEQ ID NO 9
<211> LENGTH: 99
<212> TYPE: PRT
<213> ORGANISM: Artificial sequence
<220> FEATURE:
<223> OTHER INFORMATION: Link_TSG-6

<400> SEQUENCE: 9

Met Gly Val Tyr His Arg Glu Ala Arg Ser Gly Lys Tyr Lys Leu Thr
  1               5                  10                  15

Tyr Ala Glu Ala Lys Ala Val Cys Glu Phe Glu Gly Gly His Leu Ala
             20                  25                  30

Thr Tyr Lys Gln Leu Glu Ala Ala Arg Lys Ile Gly Phe His Val Cys
         35                  40                  45

Ala Ala Gly Trp Met Ala Lys Gly Arg Val Gly Tyr Pro Ile Val Lys
     50                  55                  60

Pro Gly Pro Asn Cys Gly Phe Gly Lys Thr Gly Ile Ile Asp Tyr Gly
 65                  70                  75                  80

Ile Arg Leu Asn Arg Ser Glu Arg Trp Asp Ala Tyr Cys Tyr Asn Pro
                 85                  90                  95
```

-continued

His Ala Lys

<210> SEQ ID NO 10
<211> LENGTH: 149
<212> TYPE: PRT
<213> ORGANISM: Homo sapiens

<400> SEQUENCE: 10

```
Asn Pro His Ala Lys Glu Cys Gly Gly Val Phe Thr Asp Pro Lys Gln
1               5                   10                  15

Ile Phe Lys Ser Pro Gly Phe Pro Asn Glu Tyr Glu Asp Asn Gln Ile
            20                  25                  30

Cys Tyr Trp His Ile Arg Leu Lys Tyr Gly Gln Arg Ile His Leu Ser
        35                  40                  45

Phe Leu Asp Phe Asp Leu Glu Asp Asp Pro Gly Cys Leu Ala Asp Tyr
    50                  55                  60

Val Glu Ile Tyr Asp Ser Tyr Asp Asp Val His Gly Phe Val Gly Arg
65                  70                  75                  80

Tyr Cys Gly Asp Glu Leu Pro Asp Asp Ile Ile Ser Thr Gly Asn Val
                85                  90                  95

Met Thr Leu Lys Phe Leu Ser Asp Ala Ser Val Thr Ala Gly Gly Phe
            100                 105                 110

Gln Ile Lys Tyr Val Ala Met Asp Pro Val Ser Lys Ser Ser Gln Gly
        115                 120                 125

Lys Asn Thr Ser Thr Thr Ser Thr Gly Asn Lys Asn Phe Leu Ala Gly
    130                 135                 140

Arg Phe Ser His Leu
145
```

<210> SEQ ID NO 11
<211> LENGTH: 149
<212> TYPE: PRT
<213> ORGANISM: Homo sapiens

<400> SEQUENCE: 11

```
Asn Pro His Ala Lys Glu Cys Gly Gly Val Phe Thr Asp Pro Lys Arg
1               5                   10                  15

Ile Phe Lys Ser Pro Gly Phe Pro Asn Glu Tyr Glu Asp Asn Gln Ile
            20                  25                  30

Cys Tyr Trp His Ile Arg Leu Lys Tyr Gly Gln Arg Ile His Leu Ser
        35                  40                  45

Phe Leu Asp Phe Asp Leu Glu Asp Asp Pro Gly Cys Leu Ala Asp Tyr
    50                  55                  60

Val Glu Ile Tyr Asp Ser Tyr Asp Asp Val His Gly Phe Val Gly Arg
65                  70                  75                  80

Tyr Cys Gly Asp Glu Leu Pro Asp Asp Ile Ile Ser Thr Gly Asn Val
                85                  90                  95

Met Thr Leu Lys Phe Leu Ser Asp Ala Ser Val Thr Ala Gly Gly Phe
            100                 105                 110

Gln Ile Lys Tyr Val Ala Met Asp Pro Val Ser Lys Ser Ser Gln Gly
        115                 120                 125

Lys Asn Thr Ser Thr Thr Ser Thr Gly Asn Lys Asn Phe Leu Ala Gly
    130                 135                 140

Arg Phe Ser His Leu
145
```

<210> SEQ ID NO 12
<211> LENGTH: 471
<212> TYPE: DNA
<213> ORGANISM: Artificial sequence
<220> FEATURE:
<223> OTHER INFORMATION: CUB_C_TSG6
<220> FEATURE:
<221> NAME/KEY: CDS
<222> LOCATION: (14)..(463)

<400> SEQUENCE: 12

```
aggagatata cat atg aac cca cac gca aag gag tgt ggt ggc gtc ttt        49
               Met Asn Pro His Ala Lys Glu Cys Gly Gly Val Phe
                1               5                  10 aca gat cca aag cga att ttt aaa tct cca ggc ttc cca aat gag tac        97
Thr Asp Pro Lys Arg Ile Phe Lys Ser Pro Gly Phe Pro Asn Glu Tyr
         15                  20                  25 gaa gat aac caa atc tgc tac tgg cac att aga ctc aag tat ggt cag       145
Glu Asp Asn Gln Ile Cys Tyr Trp His Ile Arg Leu Lys Tyr Gly Gln
 30                  35                  40 cgt att cac ctg agt ttt tta gat ttt gac ctt gaa gat gac cca ggt       193
Arg Ile His Leu Ser Phe Leu Asp Phe Asp Leu Glu Asp Asp Pro Gly
45                  50                  55                  60 tgc ttg gct gat tat gtt gaa ata tat gac agt tac gat gat gtc cat       241
Cys Leu Ala Asp Tyr Val Glu Ile Tyr Asp Ser Tyr Asp Asp Val His
                 65                  70                  75 ggc ttt gtg gga aga tac tgt gga gat gag ctt cca gat gac atc atc       289
Gly Phe Val Gly Arg Tyr Cys Gly Asp Glu Leu Pro Asp Asp Ile Ile
             80                  85                  90 agt aca gga aat gtc atg acc ttg aag ttt cta agt gat gct tca gtg       337
Ser Thr Gly Asn Val Met Thr Leu Lys Phe Leu Ser Asp Ala Ser Val
         95                 100                 105 aca gct gga ggt ttc caa atc aaa tat gtt gca atg gat cct gta tcc       385
Thr Ala Gly Gly Phe Gln Ile Lys Tyr Val Ala Met Asp Pro Val Ser
    110                 115                 120 aaa tcc agt caa gga aaa aat aca agt act act tct act gga aat aaa       433
Lys Ser Ser Gln Gly Lys Asn Thr Ser Thr Thr Ser Thr Gly Asn Lys
125                 130                 135                 140 aac ttt tta gct gga aga ttt agc cac tta taa attcg                    471
Asn Phe Leu Ala Gly Arg Phe Ser His Leu
                145                 150
```

<210> SEQ ID NO 13
<211> LENGTH: 150
<212> TYPE: PRT
<213> ORGANISM: Artificial sequence
<220> FEATURE:
<223> OTHER INFORMATION: CUB_C_TSG6

<400> SEQUENCE: 13

```
Met Asn Pro His Ala Lys Glu Cys Gly Gly Val Phe Thr Asp Pro Lys
  1               5                  10                  15

Arg Ile Phe Lys Ser Pro Gly Phe Pro Asn Glu Tyr Glu Asp Asn Gln
             20                  25                  30

Ile Cys Tyr Trp His Ile Arg Leu Lys Tyr Gly Gln Arg Ile His Leu
         35                  40                  45

Ser Phe Leu Asp Phe Asp Leu Glu Asp Asp Pro Gly Cys Leu Ala Asp
     50                  55                  60

Tyr Val Glu Ile Tyr Asp Ser Tyr Asp Asp Val His Gly Phe Val Gly
 65                  70                  75                  80

Arg Tyr Cys Gly Asp Glu Leu Pro Asp Asp Ile Ile Ser Thr Gly Asn
```

```
                      85                  90                  95
Val Met Thr Leu Lys Phe Leu Ser Asp Ala Ser Val Thr Ala Gly Gly
            100                 105                 110

Phe Gln Ile Lys Tyr Val Ala Met Asp Pro Val Ser Lys Ser Ser Gln
            115                 120                 125

Gly Lys Asn Thr Ser Thr Ser Thr Gly Asn Lys Asn Phe Leu Ala
            130                 135                 140

Gly Arg Phe Ser His Leu
145                 150

<210> SEQ ID NO 14
<211> LENGTH: 1356
<212> TYPE: DNA
<213> ORGANISM: Homo sapiens
<220> FEATURE:
<221> NAME/KEY: CDS
<222> LOCATION: (95)..(1300)

<400> SEQUENCE: 14
gtatatataa cgtgatgagc gtacgggtgc ggagacgcac cggagcgctc gcccagccgc     60
cgyctccaag cccctgaggt ttccggggac caca atg aac aag ttg ctg tgc tgc    115
                                      Met Asn Lys Leu Leu Cys Cys
                                       1               5 gcg ctc gtg ttt ctg gac atc tcc att aag tgg acc acc cag gaa acg      163
Ala Leu Val Phe Leu Asp Ile Ser Ile Lys Trp Thr Thr Gln Glu Thr
            10                  15                  20 ttt cct cca aag tac ctt cat tat gac gaa gaa acc tct cat cag ctg      211
Phe Pro Pro Lys Tyr Leu His Tyr Asp Glu Glu Thr Ser His Gln Leu
        25                  30                  35 ttg tgt gac aaa tgt cct cct ggt acc tac cta aaa caa cac tgt aca      259
Leu Cys Asp Lys Cys Pro Pro Gly Thr Tyr Leu Lys Gln His Cys Thr
 40                  45                  50                  55 gca aag tgg aag acc gtg tgc gcc cct tgc cct gac cac tac tac aca      307
Ala Lys Trp Lys Thr Val Cys Ala Pro Cys Pro Asp His Tyr Tyr Thr
                 60                  65                  70 gac agc tgg cac acc agt gac gag tgt cta tac tgc agc ccc gtg tgc      355
Asp Ser Trp His Thr Ser Asp Glu Cys Leu Tyr Cys Ser Pro Val Cys
             75                  80                  85 aag gag ctg cag tac gtc aag cag gag tgc aat cgc acc cac aac cgc      403
Lys Glu Leu Gln Tyr Val Lys Gln Glu Cys Asn Arg Thr His Asn Arg
         90                  95                 100 gtg tgc gaa tgc aag gaa ggg cgc tac ctt gag ata gag ttc tgc ttg      451
Val Cys Glu Cys Lys Glu Gly Arg Tyr Leu Glu Ile Glu Phe Cys Leu
    105                 110                 115 aaa cat agg agc tgc cct cct gga ttt gga gtg gtg caa gct gga acc      499
Lys His Arg Ser Cys Pro Pro Gly Phe Gly Val Val Gln Ala Gly Thr
120                 125                 130                 135 cca gag cga aat aca gtt tgc aaa aga tgt cca gat ggg ttc ttc tca      547
Pro Glu Arg Asn Thr Val Cys Lys Arg Cys Pro Asp Gly Phe Phe Ser
                140                 145                 150 aat gag acg tca tct aaa gca ccc tgt aga aaa cac aca aat tgc agt      595
Asn Glu Thr Ser Ser Lys Ala Pro Cys Arg Lys His Thr Asn Cys Ser
            155                 160                 165 gtc ttt ggt ctc ctg cta act cag aaa gga aat gca aca cac gac aac      643
Val Phe Gly Leu Leu Leu Thr Gln Lys Gly Asn Ala Thr His Asp Asn
        170                 175                 180 ata tgt tcc gga aac agt gaa tca act caa aaa tgt gga ata gat gtt      691
Ile Cys Ser Gly Asn Ser Glu Ser Thr Gln Lys Cys Gly Ile Asp Val
    185                 190                 195
```

-continued

| | | |
|---|---|---|
| acc ctg tgt gag gag gca ttc ttc agg ttt gct gtt cct aca aag ttt<br>Thr Leu Cys Glu Glu Ala Phe Phe Arg Phe Ala Val Pro Thr Lys Phe<br>200                        205                         210                   215 | 739 |
| acg cct aac tgg ctt agt gtc ttg gta gac aat ttg cct ggc acc aaa<br>Thr Pro Asn Trp Leu Ser Val Leu Val Asp Asn Leu Pro Gly Thr Lys<br>                 220                       225                       230 | 787 |
| gta aac gca gag agt gta gag agg ata aaa cgg caa cac agc tca caa<br>Val Asn Ala Glu Ser Val Glu Arg Ile Lys Arg Gln His Ser Ser Gln<br>                    235                       240                     245 | 835 |
| gaa cag act ttc cag ctg ctg aag tta tgg aaa cat caa aac aaa gcc<br>Glu Gln Thr Phe Gln Leu Leu Lys Leu Trp Lys His Gln Asn Lys Ala<br>250                        255                         260 | 883 |
| caa gat ata gtc aag aag atc atc caa gat att gac ctc tgt gaa aac<br>Gln Asp Ile Val Lys Lys Ile Ile Gln Asp Ile Asp Leu Cys Glu Asn<br>265                        270                       275 | 931 |
| agc gtg cag cgg cac att gga cat gct aac ctc acc ttc gag cag ctt<br>Ser Val Gln Arg His Ile Gly His Ala Asn Leu Thr Phe Glu Gln Leu<br>280                        285                     290                   295 | 979 |
| cgt agc ttg atg gaa agc tta ccg gga aag aaa gtg gga gca gaa gac<br>Arg Ser Leu Met Glu Ser Leu Pro Gly Lys Lys Val Gly Ala Glu Asp<br>                   300                       305                     310 | 1027 |
| att gaa aaa aca ata aag gca tgc aaa ccc agt gac cag atc ctg aag<br>Ile Glu Lys Thr Ile Lys Ala Cys Lys Pro Ser Asp Gln Ile Leu Lys<br>315                        320                       325 | 1075 |
| ctg ctc agt ttg tgg cga ata aaa aat ggc gac caa gac acc ttg aag<br>Leu Leu Ser Leu Trp Arg Ile Lys Asn Gly Asp Gln Asp Thr Leu Lys<br>330                        335                       340 | 1123 |
| ggc cta atg cac gca cta aag cac tca aag acg tac cac ttt ccc aaa<br>Gly Leu Met His Ala Leu Lys His Ser Lys Thr Tyr His Phe Pro Lys<br>345                        350                       355 | 1171 |
| act gtc act cag agt cta aag aag acc atc agg ttc ctt cac agc ttc<br>Thr Val Thr Gln Ser Leu Lys Lys Thr Ile Arg Phe Leu His Ser Phe<br>360                        365                     370                   375 | 1219 |
| aca atg tac aaa ttg tat cag aag tta ttt tta gaa atg ata ggt aac<br>Thr Met Tyr Lys Leu Tyr Gln Lys Leu Phe Leu Glu Met Ile Gly Asn<br>                   380                       385                     390 | 1267 |
| cag gtc caa tca gta aaa ata agc tgc tta taa ctggaaatgg ccattgagct<br>Gln Val Gln Ser Val Lys Ile Ser Cys Leu<br>395                        400 | 1320 |
| gtttcctcac aattggcgag atcccatgga tgataa | 1356 |

<210> SEQ ID NO 15
<211> LENGTH: 401
<212> TYPE: PRT
<213> ORGANISM: Homo sapiens

<400> SEQUENCE: 15

Met Asn Lys Leu Leu Cys Cys Ala Leu Val Phe Leu Asp Ile Ser Ile
1               5                      10                     15

Lys Trp Thr Thr Gln Glu Thr Phe Pro Pro Lys Tyr Leu His Tyr Asp
                   20                       25                     30

Glu Glu Thr Ser His Gln Leu Leu Cys Asp Lys Cys Pro Pro Gly Thr
                 35                       40                     45

Tyr Leu Lys Gln His Cys Thr Ala Lys Trp Lys Thr Val Cys Ala Pro
 50                    55                       60

Cys Pro Asp His Tyr Tyr Thr Asp Ser Trp His Thr Ser Asp Glu Cys
65               70                     75                     80

Leu Tyr Cys Ser Pro Val Cys Lys Glu Leu Gln Tyr Val Lys Gln Glu
                   85                       90                     95

```
Cys Asn Arg Thr His Asn Arg Val Cys Glu Cys Lys Glu Gly Arg Tyr
            100                 105                 110
Leu Glu Ile Glu Phe Cys Leu Lys His Arg Ser Cys Pro Pro Gly Phe
            115                 120                 125
Gly Val Val Gln Ala Gly Thr Pro Glu Arg Asn Thr Val Cys Lys Arg
            130                 135                 140
Cys Pro Asp Gly Phe Phe Ser Asn Glu Thr Ser Ser Lys Ala Pro Cys
145                 150                 155                 160
Arg Lys His Thr Asn Cys Ser Val Phe Gly Leu Leu Leu Thr Gln Lys
                165                 170                 175
Gly Asn Ala Thr His Asp Asn Ile Cys Ser Gly Asn Ser Glu Ser Thr
            180                 185                 190
Gln Lys Cys Gly Ile Asp Val Thr Leu Cys Glu Glu Ala Phe Phe Arg
            195                 200                 205
Phe Ala Val Pro Thr Lys Phe Thr Pro Asn Trp Leu Ser Val Leu Val
            210                 215                 220
Asp Asn Leu Pro Gly Thr Lys Val Asn Ala Glu Ser Val Glu Arg Ile
225                 230                 235                 240
Lys Arg Gln His Ser Ser Gln Glu Gln Thr Phe Gln Leu Leu Lys Leu
                245                 250                 255
Trp Lys His Gln Asn Lys Ala Gln Asp Ile Val Lys Lys Ile Ile Gln
                260                 265                 270
Asp Ile Asp Leu Cys Glu Asn Ser Val Gln Arg His Ile Gly His Ala
            275                 280                 285
Asn Leu Thr Phe Glu Gln Leu Arg Ser Leu Met Glu Ser Leu Pro Gly
            290                 295                 300
Lys Lys Val Gly Ala Glu Asp Ile Glu Lys Thr Ile Lys Ala Cys Lys
305                 310                 315                 320
Pro Ser Asp Gln Ile Leu Lys Leu Leu Ser Leu Trp Arg Ile Lys Asn
                325                 330                 335
Gly Asp Gln Asp Thr Leu Lys Gly Leu Met His Ala Leu Lys His Ser
            340                 345                 350
Lys Thr Tyr His Phe Pro Lys Thr Val Thr Gln Ser Leu Lys Lys Thr
            355                 360                 365
Ile Arg Phe Leu His Ser Phe Thr Met Tyr Lys Leu Tyr Gln Lys Leu
            370                 375                 380
Phe Leu Glu Met Ile Gly Asn Gln Val Gln Ser Val Lys Ile Ser Cys
385                 390                 395                 400
Leu
```

METHOD OF TREATING BONE DISORDERS USING TSG-6

CROSS-REFERENCE TO RELATED APPLICATIONS

This application claims priority under 35 U.S.C. § 371 from international application PCT/GB2007/000772, filed Mar. 6, 2007, which claims priority from Great Britain Application No. 0604460.6, filed Mar. 6, 2006.

FIELD OF THE INVENTION

The present invention relates to a method for treating or preventing diseases or conditions associated with bone resorption by osteoclasts.

BACKGROUND OF THE INVENTION

Tumour necrosis factor (TNF)-stimulated gene 6 (TSG-6) is an inflammation-induced protein with protective roles in arthritis. TSG-6, the ~35 kDa secreted product of TNF-stimulated gene-6, is expressed in response to inflammatory mediators and growth factors, where there is believed to be little or no constitutive expression of the protein in healthy tissues (Milner & Day (2003) *J. Cell Sci.* 116, 1863-1873).

There is increasing evidence that TSG-6, whilst induced in response to inflammation, has anti-inflammatory and chondroprotective properties, making it an endogenous inhibitor of joint destruction. In this regard, TSG-6 has been found to have diverse biological activities, such as inhibition of neutrophil migration, down-regulation of plasmin activity, and the cross-linking of hyaluronan (HA) chains, which are all likely to contribute to its chondroprotective properties (Wisniewski et al. (1996) *J. Immunol.* 156, 1609-1615; and Milner et al., (2006) *Biochem. Soc. Trans.* 34, 446-450).

TSG-6, which is comprised almost entirely of contiguous Link and CUB_C domains, binds to a variety of protein and glycosaminoglycan ligands (including HA, chondroitin-4-sulphate, aggrecan, inter-α-inhibitor (IαI), pentraxin-3, thrombospondin-1, fibronectin and heparin/heparan sulphate), where the majority of these interactions are mediated through its Link module domain. Mutagenesis studies have revealed that at least three non-overlapping ligand-binding surfaces are present on the Link module (Mahoney et al. (2005) *J. Biol. Chem.* 280, 27044-27055; and Kuznetsova et al. (2005) *J. Biol. Chem.* 280, 30899-30908). To date, the only ligand identified for the CUB_C domain is fibronectin (D J Mahoney & A J Day, unpublished data). In addition, this domain contains a divalent cation-binding site (Rugg et al. (2005) *J. Biol. Chem.* 280, 25674-25686).

TSG-6 has been detected in the context of inflammatory diseases such as rheumatoid arthritis (RA), where it is present in the synovial fluid, cartilage and synovia. It is likely that TSG-6 is produced locally in joint tissues, since its expression can be induced in cultured human chondrocytes by TNF, IL-1, IL-6, TGF-β and PDGF and it is constitutively expressed by synoviocytes from RA patients, where its production is further enhanced by treatment with IL-1, TNF and IL-17 (Milner et al., (2006) *Biochem. Soc. Trans.* 34, 446-450).

Importantly, a number of recent studies have revealed that TSG-6 has a protective role in experimental models of arthritis. For example, in a model of collagen-induced arthritis (CIA; an autoimmune polyarthritis with a histopathology similar to human RA), there was delayed onset of symptoms and reduction of both disease incidence and joint inflammation/destruction in TSG-6 transgenic mice or wild-type mice treated systemically with recombinant human TSG-6 (Mindrescu et al. (2000) *Arthritis Rheum.* 43, 2668-2677; and Mindrescu et al. (2002) *Arthritis Rheum.* 46, 2453-2464). In TSG-6 transgenic animals, an ameliorative effect comparable to anti-TNF-antibody treatment was seen. Furthermore, in cartilage-specific TSG-6 transgenic mice, the instigation of antigen-induced arthritis (AIA; a model of monoarticular arthritis) resulted in delayed cartilage damage compared to controls, with reduced degradation of aggrecan by MMPs and aggrecanase, and there was evidence of cartilage regeneration, 4-5 weeks after the onset of disease in these animals (Glant et al. (2002) *Arthritis Rheum.* 46, 2207-2218). Similar chondroprotective effects were seen in wild-type mice where recombinant murine TSG-6 was injected directly into the affected joint in AIA or intravenously in proteoglycan-induced arthritis (PGIA; a model of human RA) (Bárdos et al. (2001) *Am. J. Pathol.* 159, 1711-1721).

The anti-inflammatory and chondroprotective effects of TSG-6 observed in these studies are likely due to more than one mechanism. Most importantly, TSG-6 is a potent inhibitor of neutrophil extravasation in vivo and has also been implicated in the inhibition of the protease network through its potentiation of the anti-plasmin activity of IαI, where plasmin is a key regulator of proteolysis during inflammation, e.g., via its activation of MMPs (Wisniewski et al. (1996) *J. Immunol.* 156, 1609-1615; and Getting et al. (2002) *J. Biol. Chem.* 277, 51068-51076). In this regard, mice lacking TSG-6 develop an accelerated and much more severe form of PGIA than controls, with rapid and extensive cartilage degradation and bone erosion (Szántó et al. (2004) *Arthritis Rheum.* 50, 3012-3022). Increased neutrophil infiltration and plasmin activity were suggested to account for these effects in the TSG-6$^{-/-}$ mice.

SUMMARY OF THE INVENTION

The present inventors have shown that TSG-6 inhibits bone resorption by osteoclasts. Osteoclasts are large, multinucleated cells that are derived from the monocyte/macrophage lineage and degrade bone matrix and mineral in the process of bone resorption. The present inventors have also shown that the absence of TSG-6 in TSG-6 knockout mice leads to increased bone resorption by osteoclasts. The present inventors have shown that TSG-6 is useful in treating and preventing a bone disease or condition associated with bone resorption by osteoclasts. The present inventors have also shown that administration of osteoprotegerin (OPG) in combination with TSG-6 results in a synergistic effect. A combination of TSG-6 and OPG inhibit bone resorption by osteoclasts to a greater extent than the sum of each factor alone.

In accordance with the present invention, there is thus provided the use of a TSG-6 polypeptide, or a polynucleotide encoding a TSG-6 polypeptide, in the manufacture of a medicament for the treatment or prevention of a bone disease or condition associated with bone resorption by osteoclasts. In a preferred embodiment, the medicament is administered in combination with a therapeutically or prophylactically effective amount of an OPG polypeptide, a polynucleotide encoding an OPG polypeptide or an OPG mimetic.

The present invention also provides a method of treating or preventing a bone disease or condition associated with bone resorption by osteoclasts in a subject in need thereof, the method comprising administering to the subject a therapeutically or prophylactically effective amount of an TSG-6 polypeptide, or a polynucleotide encoding an TSG-6 polypeptide. In a preferred embodiment, the method further comprises administering to the subject a therapeutically or prophylactically effective amount of an OPG polypeptide, a polynucleotide encoding an OPG polypeptide or an OPG mimetic.

The invention further provides:
use of:
(a) a TSG-6 polypeptide, or a polynucleotide encoding a TSG-6 polypeptide; and
(b) an OPG polypeptide, a polynucleotide encoding an OPG polypeptide or an OPG mimetic;
in the manufacture of a medicament for the treatment or prevention of a disease or condition associated with bone resorption by osteoclasts;
a product containing:
(a) a TSG-6 polypeptide, or a polynucleotide encoding a TSG-6 polypeptide; and
(b) an OPG polypeptide, a polynucleotide encoding an OPG polypeptide or an OPG mimetic;
for simultaneous, separate or sequential use in the treatment or prevention of a disease or condition associated with bone resorption by osteoclasts; and use of:
(a) a TSG-6 polypeptide, or a polynucleotide encoding a TSG-6 polypeptide; or
(b) an OPG polypeptide, a polynucleotide encoding an OPG polypeptide or an OPG mimetic;
in the manufacture of a medicament for the treatment or prevention by combination therapy of a disease or condition associated with bone resorption by osteoclasts, wherein (a) and (b) are administered simultaneously, separately or sequentially.

One advantage of the present invention is that the TSG-6 polypeptide or polynucleotide can have anti-inflammatory and/or chondroprotective effects in addition to inhibiting bone resorption by osteoclasts. These anti-inflammatory and/or chondroprotective effects can result from the inhibition of neutrophil migration, the down-regulation of plasmin activity and/or the TSG-6-mediated cross-linking of HA chains.

BRIEF DESCRIPTION OF THE SEQUENCES

Figure 1:
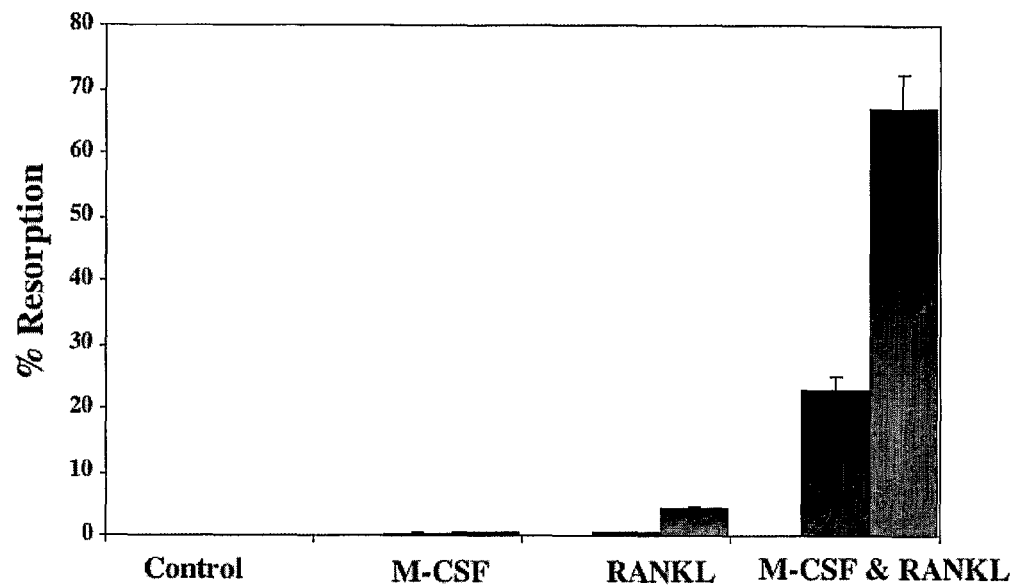
FIG. 1 shows the effect of TSG-6 on osteoclastogenesis. sRANKL/M-CSF-mediated human osteoclast formation was determined in the absence (lighter bars on the right hand side) and presence (darker bars on the left hand side) of recombinant human TSG-6 (25 ng/ml (0.8 nM)). Data (n=8 dentine slices) are expressed as mean values±S.E. of 2 independent experiments, of 4 replicates each.

SEQ ID NO: 1 shows the nucleic acid sequence encoding the full-length Q144 allotypic variant of human TSG-6.

SEQ ID NO: 2 shows the amino acid sequence of full-length Q144 allotypic variant of human TSG-6. This allotypic variant has a glutamine residue (Q) at position 144. It is the most common allotypic variant and is found in approximately 86% of the Caucasian population (Nentwich et al. (2002) 277, 15354-15362).

SEQ ID NO: 3 (residues 18-277 of SEQ ID NO: 2) shows the amino acid sequence of the Q144 allotypic variant of human TSG-6 without the signal sequence.

SEQ ID NO: 4 shows the nucleic acid sequence encoding the full-length R144 allotypic variant of human TSG-6.

SEQ ID NO: 5 shows the amino acid sequence of full-length R144 allotypic variant of human TSG-6. This allotypic variant has an arginine residue (R) at position 144. It is the less common allotypic variant and is found in approximately 14% of the Caucasian population (Nentwich et al. (2002) 277, 15354-15362).

SEQ ID NO: 6 (residues 18-277 of SEQ ID NO: 5) shows the amino acid sequence of the R144 allotypic variant of human TSG-6 without the signal sequence.

SEQ ID NO: 7 (residues 37-128 of SEQ ID NOs: 2 and 5) shows the amino acid sequence of the Link module of human TSG-6.

SEQ ID NO: 8 shows the nucleic acid sequence encoding Link_TSG6 used in the Examples (Day et al. (1996) *Protein Expr. Pruif.* 8, 1-16).

SEQ ID NO: 9 shows the amino acid sequence of Link_TSG6 used in the Examples. Residues 3-95 of SEQ ID NO: 9 correspond to SEQ ID NO: 7 (residues 37-128 of SEQ ID NOs: 2 and 5). The initiating methionine (Met-1) is removed on expression of Link_TSG6 (Day et al. (1996) *Protein Expr. Pruif,* 8, 1-16).

SEQ ID NO: 10 (residues 129-277 of SEQ ID NO: 2) shows the amino acid sequence of the CUB_C domain of the Q144 allotypic variant of human TSG-6.

SEQ ID NO: 11 (residues 129-277 of SEQ ID NO: 5) shows the amino acid sequence of the CUB_C domain of the R144 allotypic variant of human TSG-6.

SEQ ID NO: 12 shows the nucleic acid sequence encoding the CUB_C_TSG6 used in the Examples.

SEQ ID NO: 13 shows the amino acid sequence of CUB_C_TSG6 used in the Examples. Residues 2-150 of SEQ ID NO: 13 correspond to SEQ ID NO: 11 (residues 129-277 of SEQ ID NO: 5). The initiating methionine (Met-1) is not removed on expression of CUB_C_TSG6 (A J Day, unpublished data).

SEQ ID NO: 14 shows the nucleic acid sequence encoding full-length human OPG.

SEQ ID NO: 15 shows the amino acid sequence of full-length human OPG.

DETAILED DESCRIPTION OF THE INVENTION

The present invention provides a method for treating or preventing bone diseases or conditions associated with bone resorption by osteoclasts, which method comprises administering to a subject a TSG-6 polypeptide or a polynucleotide encoding a TSG-6 polypeptide. In a preferred embodiment, the method further comprises administering to the subject a therapeutically or prophylactically effective amount of an OPG polypeptide, a polynucleotide encoding an OPG polypeptide or an OPG mimetic.

TSG-6 Polypeptides

The TSG-6 polypeptide is preferably human TSG-6, or a variant or fragment of human TSG-6 which retains RANKL binding activity. The TSG-6 polypeptide has the ability to inhibit bone resorption by osteoclasts. The variant can be a TSG-6 polypeptide from another organism, such as a primate, a mouse or a rat.

The TSG-6 polypeptide preferably comprises:
(a) the amino acid sequence of SEQ ID NO: 2 or 5;
(b) a variant thereof having at least 50% identity to the amino acid sequence of SEQ ID NO: 2 or 5 and having receptor activator of NFκB ligand (RANKL) binding activity; or
(c) a fragment of either (a) or (b) having RANKL binding activity.

Preferably, the polypeptide comprises, or consists of, the sequence of SEQ ID NO:2 or 5.

The TSG-6 polypeptide can additionally lack a signal sequence. Accordingly, the TSG-6 polypeptide preferably comprises:
(a) the amino acid sequence of SEQ ID NO: 3 or 6;
(b) a variant thereof having at least 50% identity to the amino acid sequence of SEQ ID NO: 3 or 6 and having RANKL binding activity; or
(c) a fragment of either (a) or (b) having RANKL binding activity.

The TSG-6 polypeptide preferably consists of the sequence shown in SEQ ID NO: 3 or 6.

The TSG-6 polypeptide can additionally lack the CUB_C domain. The CUB_C domain corresponds to residues 129-277 of SEQ ID NOs: 2 and 5. The TSG-6 polypeptide can comprise only the Link module of human TSG-6. The Link module corresponds to residues 37-128 of SEQ ID NOs: 2 and 5 and is shown in SEQ ID NO: 7. The Link module is responsible for the hyaluronan (HA) binding activity, chondroitin-4-sulphate binding activity, aggrecan binding activity, inter-α-inhibitor (IαI) binding activity, bikunin binding activity, versican binding activity, dermatan sulphate binding activity, pentraxin-3 binding activity, thrombospondin-1 binding activity, heparin/heparan sulphate binding activity and RANKL binding activity of TSG-6. Accordingly, the TSG-6 polypeptide preferably comprises:
(a) the amino acid sequence of SEQ ID NO: 7;
(b) a variant thereof having at least 50% identity to the amino acid sequence of SEQ ID NO: 7 and having RANKL binding activity; or
(c) a fragment of either (a) or (b) having RANKL binding activity.

The TSG-6 polypeptide preferably consists of the sequence shown in SEQ ID NO: 7.

SEQ ID NO: 9 shows a recombinant polypeptide which includes the Link module of TSG-6 (Link_TSG6). Accordingly, the TSG-6 polypeptide used in the invention preferably comprises:
(a) the amino acid sequence of SEQ ID NO: 9;
(b) a variant thereof having at least 50% identity to the amino acid sequence of SEQ ID NO: 9 and having RANKL binding activity; or
(c) a fragment of either (a) or (b) having RANKL binding activity.

The TSG-6 polypeptide preferably consists of the sequence shown in SEQ ID NO: 9.

The TSG-6 polypeptide can additionally lack the Link module. The Link module corresponds to residues 37-128 of SEQ ID NOs: 2 and 5. The TSG-6 polypeptide can comprise only the CUB_C domain of human TSG-6. The CUB_C domain corresponds to residues 129-277 of SEQ ID NOs: 2 and 5 and is shown in SEQ ID NOs: 10 and 11. The CUB module is also responsible for the fibronectin binding activity of TSG-6 and RANKL binding activity of TSG-6. Accordingly, the TSG-6 polypeptide preferably comprises:
(a) the amino acid sequence of SEQ ID NO: 10 or 11;
(b) a variant thereof having at least 50% identity to the amino acid sequence of SEQ ID NO: 10 or 11 and having RANKL binding activity; or
(c) a fragment of either (a) or (b) having RANKL binding activity.

The TSG-6 polypeptide preferably consists of the sequence shown in SEQ ID NO: 10 or 11.

SEQ ID NO: 13 shows a recombinant polypeptide which includes the CUB_C domain of TSG-6 (CUB_C_TSG-6). Accordingly, the TSG-6 polypeptide used in the invention preferably comprises:
(a) the amino acid sequence of SEQ ID NO: 13;
(b) a variant thereof having at least 50% identity to the amino acid sequence of SEQ ID NO: 13 and having RANKL binding activity; or
(c) a fragment of either (a) or (b) having RANKL binding activity.

The TSG-6 polypeptide preferably consists of the sequence shown in SEQ ID NO: 13.

Variant polypeptides are those for which the amino acid sequence varies from that in SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13, but which retain the function of TSG-6. The variant polypeptides therefore inhibit bone resorption by osteoclasts. The variant polypeptides bind to RANKL.

The variant polypeptides typically also bind to HA, chondroitin-4-sulphate, aggrecan, inter-α-inhibitor (IαI), bikunin, versican, dermatan sulphate, pentraxin-3, thrombospondin-1, heparin/heparan sulphate and/or fibronectin. The variant polypeptides can also have anti-inflammatory and/or chondroprotective effects.

The binding activity of the variant polypeptides can be modified to produce different effects in a subject treated in accordance with the invention. For instance, a variant polypeptide that is unable to bind inter-α-inhibitor (IαI) may not produce anti-inflammatory effects in the subject. Alternatively, a variant polypeptide that is unable to bind to HA may not produce chondroprotective effects in the subject.

Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13 are considered variants of the TSG-6 protein. Such variants include allelic variants and the deletion, modification or addition of single amino acids or groups of amino acids within the protein sequence, as long as the peptide maintains the basic functionality of TSG-6. The identity of variants of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13 can be measured over a region of at least 50, at least 75, at least 100, at least 150, at least 200 or at least 250 or more contiguous amino acids of the sequence shown in SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13, or more preferably over the full length of SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 11 or SEQ ID NO: 13.

Variants of the amino acid sequence of SEQ ID NO: 2, SEQ ID NO: 3, SEQ ID NO: 5, SEQ ID NO: 6, SEQ ID NO: 7 or SEQ ID NO: 9 preferably contain the residues shown to be essential for hyaluronan binding in Mahoney et al. (2001) *J. Biol. Chem.* 276, 22764-22771 and Blundell et al. (2003) *J. Biol. Chem.* 278, 49261-49270. Variants of the amino acid sequence of SEQ ID NO: 2 or 5 preferably contain the residues Lys-46 and/or Tyr-47 and/or Tyr-94 and/or Phe-105 and/or Tyr-113 of SEQ ID NO: 2 or 5. Most preferably, the variant of SEQ ID NO: 2 or 5 contains each of residues Lys-46, Tyr-47, Tyr-94, Phe-105 and Tyr-113 of SEQ ID NO: 2 or 5.

Variants of the amino acid sequence of SEQ ID NO: 3 or 6 preferably contain the residues Lys-29 and/or Tyr-30 and/or Tyr-77 and/or Phe-88 and/or Tyr-96 of SEQ ID NO: 3 or 6. Most preferably, the variant of SEQ ID NO: 3 or 6 contains each of residues Lys-29, Tyr-30, Tyr-77, Phe-88 and Tyr-96 of SEQ ID NO: 3 or 6.

Variants of the amino acid sequence of SEQ ID NO: 7 preferably contain the residues Lys-10 and/or Tyr-11 and/or Tyr-58 and/or Phe-69 and/or Tyr-77 of SEQ ID NO: 7. Most preferably, the variant of SEQ ID NO: 7 contains each of residues Lys-10, Tyr-11, Tyr-58, Phe-69 and Tyr-77 of SEQ ID NO: 7.

Variants of the amino acid sequence of SEQ ID NO: 9 preferably contain the residues Lys-12 and/or Tyr-13 and/or Tyr-60 and/or Phe-71 and/or Tyr-79 of SEQ ID NO: 9. Most preferably, the variant of SEQ ID NO: 9 contains each of residues Lys-12, Tyr-13, Tyr-60, Phe-71 and Tyr-79 of SEQ ID NO: 9.

Amino acid identity may be calculated using any suitable algorithm. For example the UWGCG Package provides the BESTFIT program which can be used to calculate homology (for example used on its default settings) (Devereux et al (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul (1993) *J Mol Evol* 36, 290-300; Altschul, et al. (1990) *J Mol Biol* 215, 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89, 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90, 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 5, 10, 20, 30, 50 or more mutations (which can be substitutions, deletions or insertions of amino acids). For example, from 1 to 50, 2 to 30, 3 to 20 or 5 to 10 amino acid substitutions, deletions or insertions can be made. The modified polypeptide generally retains RANKL binding. The substitutions are preferably conservative substitutions, for example according to the following Table. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The fragment of the TSG-6 polypeptide used in the invention retains the function of TSG-6. The fragment polypeptides therefore inhibit bone resorption by osteoclasts. The fragment polypeptides bind to RANKL.

The fragment polypeptides typically also bind to HA, chondroitin-4-sulphate, aggrecan, inter-α-inhibitor (IαI), bikunin, versican, dermatan sulphate, pentraxin-3, thrombospondin-1, heparin/heparan sulphate and/or fibronectin. The fragment polypeptides can also have anti-inflammatory and/or chondroprotective effects.

The binding activity of the fragment polypeptides can be modified to produce different effects in a subject treated in accordance with the invention. For instance, a fragment polypeptide that is unable to bind inter-α-inhibitor (IαI) may not produce anti-inflammatory effects in the subject. Alternatively, a fragment polypeptide that is unable to bind to HA may not produce chondroprotective effects in the subject.

The fragment of the TSG-6 polypeptide used in the invention is typically at least 10, for example at least 15, 20, 25, 30, 40, 50, 60, 70, 80, 90 or more amino acids in length, up to 100, 150, 200 or 250 amino acids in length, as long as it retains the RANKL binding activity of TSG-6. Preferably, the fragment of the TSG-6 polypeptide includes the sequence shown in SEQ ID NO: 7. Fragments of the amino acid sequence of SEQ ID NO: 2, SEQ ID NO: 3, SEQ ID NO: 5, SEQ ID NO: 6, SEQ ID NO: 7 or SEQ ID NO: 9 preferably contain the residues shown to be essential for hyaluronan binding in Mahoney et al. (2001) *J. Biol. Chem.* 276, 22764-22771 and Blundell et al. (2003) *J. Biol. Chem.* 278, 49261-49270. Fragments of the amino acid sequence of SEQ ID NO: 2 or 5 preferably contain the residues Lys-46 and/or Tyr-47 and/or Tyr-94 and/or Phe-105 and/or Tyr-113 of SEQ ID NO: 2 or 5. Most preferably, the fragment of SEQ ID NO: 2 or 5 contains each of residues Lys-46, Tyr-47, Tyr-94, Phe-105 and Tyr-113 of SEQ ID NO: 2 or 5.

Fragments of the amino acid sequence of SEQ ID NO: 7 preferably contain the residues Lys-10 and/or Tyr-11 and/or Tyr-58 and/or Phe-69 and/or Tyr-77 of SEQ ID NO: 7. Most preferably, the fragment of SEQ ID NO: 7 contains each of residues Lys-10, Tyr-11, Tyr-58, Phe-69 and Tyr-77 of SEQ ID NO: 7.

Fragments of the amino acid sequence of SEQ ID NO: 9 preferably contain the residues Lys-12 and/or Tyr-13 and/or Tyr-60 and/or Phe-71 and/or Tyr-79 of SEQ ID NO: 9. Most preferably, the fragment of SEQ ID NO: 9 contains each of residues Lys-12, Tyr-13, Tyr-60, Phe-71 and Tyr-79 of SEQ ID NO: 9.

A preferred fragment for use in the invention is residues 36-133 of SEQ ID NO: 1.

The TSG-6 polypeptides used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

The RANKL binding activity can be determined by means of a suitable assay. For example, the RANKL binding activity of a TSG-6 polypeptide can be determined using the method described in the Examples. Suitable assays for determining the ability of a TSG-6 polypeptide to bind to HA, chondroitin-4-sulphate, aggrecan, inter-α-inhibitor (IαI), bikunin, versican, dermatan sulphate, pentraxin-3, thrombospondin-1, heparin/heparan sulphate and fibronectin are well-known in the art (Getting et al. (2002) *J. Biol. Chem.* 277, 51068-51076; Mahoney et al. (2005) *J. Biol. Chem.* 280, 27044-27055; Salustri et al. (2004) *Development* 131, 1577-1586; Parkar et al. (1997) *FEBS Lett.* 410, 413-417; Parkar et al. (1998) *FEBS Lett.* 428, 171-176; Mahoney et al. (2001) *J. Biol. Chem.* 276, 22764-22771; Nentwich et al. (2002) *J. Biol. Chem.* 277, 15354-15362; and Kuznetsova et al. (2005) *J. Biol. Chem.* 280, 30899-30908).

The TSG-6 polypeptides for use in accordance with the invention display the ability to inhibit bone resorption by osteoclasts. The osteoclast inhibitory activity can be determined by means of a suitable assay. For example, the osteoclast inhibitory activity of a TSG-6 polypeptide can be determined using any of the methods described in the Example below.

TSG-6 polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

TSG-6 polypeptides for use in the present invention may be natural polypeptides. Polypeptides may be isolated from any suitable organism that expresses a TSG-6 polypeptide. The TSG-6 polypeptide may be isolated from a human or another suitable mammal, such as primates, rats or mice. Polypeptides for use in the invention may also be prepared as fragments of such isolated polypeptides.

Further, the TSG-6 polypeptides may also be made synthetically or by recombinant means. For example, a recombinant TSG-6 polypeptide may be produced by transfecting cells in culture with an expression vector comprising a nucleotide sequence encoding the polypeptide operably linked to suitable control sequences, culturing the cells, extracting and purifying the TSG-6 polypeptide produced by the cells. Methods for the recombinant production of polypeptides are well-known in the art (for example, Sambrook et al., 2001, Molecular Cloning: a laboratory manual, $3^{rd}$ edition, Cold Harbour Laboratory Press).

The amino acid sequence of TSG-6 polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

TSG-6 polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the TSG-6 polypeptides, provided that the polypeptides retain osteoclast inhibitory activity.

TSG-6 Polynucleotides

In accordance with the invention, a polynucleotide encoding a TSG-6 polypeptide, variant or fragment is used to treat or prevent a disease or condition associated with bone resorption by osteoclasts. In particular the polynucleotide preferably comprises or consists of: (a) the coding sequence of SEQ ID NO: 1, 4, 8 or 12; (b) a sequence which is degenerate as a result of the genetic code to the sequence as defined in (a); (c) a sequence having at least 60% identity to a sequence as defined in (a) or (b) and which encodes a polypeptide having RANKL binding activity; or (d) a fragment of any one of the sequences as defined in (a), (b) or (c) which encodes a polypeptide having RANKL binding activity. The polynucleotide preferably comprises or consists of: (a) the coding sequence of SEQ ID NO: 1, 4, 8 or 12; (b) a sequence which is degenerate as a result of the genetic code to the sequence as defined in (a); (c) a sequence having at least 60% identity to a sequence as defined in (a) or (b) and which encodes a polypeptide having the ability to inhibit bone resorption by osteoclasts; or (d) a fragment of any one of the sequences as defined in (a), (b) or (c) which encodes a polypeptide having the ability to inhibit bone resorption by osteoclasts.

Typically the TSG-6 polynucleotide is DNA. However, the polynucleotide may be a RNA polynucleotide. The polynucleotide may be single or double stranded, and may include within it synthetic or modified nucleotides.

A polynucleotide of the invention can typically hybridize to the coding sequence or the complement of the coding sequence of SEQ ID NO: 1, 4, 8 or 12 at a level significantly above background. Background hybridization may occur, for example, because of other DNAs present in a DNA library.

The signal level generated by the interaction between a polynucleotide of the invention and the coding sequence or complement of the coding sequence of SEQ ID NO: 1, 4, 8 or 12 is typically at least 10 fold, preferably at least 100 fold, as intense as interactions between other polynucleotides and the coding sequence of SEQ ID NO: 1, 4, 8 or 12. The intensity of interaction may be measured, for example, by radiolabelling the probe, e.g. with $^{32}$P. Selective hybridisation is typically achieved using conditions of medium to high stringency. However, such hybridisation can be carried out under any suitable conditions known in the art (see Sambrook et al., 2001, Molecular Cloning: a laboratory manual, 3$^{rd}$ edition, Cold Harbour Laboratory Press). For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 1, 4, 8 or 12 can be modified by nucleotide substitutions, for example from 1, 2 or 3 to 10, 25, 50, 100, 150 or 200 substitutions. The polynucleotide of SEQ ID NO: 1, 4, 8 or 12 can alternatively or additionally be modified by one or more insertions and/or deletions and/or by an extension at either or both ends. Additional sequences such as signal sequences may also be included. The modified polynucleotide encodes a polypeptide which has the ability to inhibit bone resorption by osteoclasts. The modified polynucleotide encodes a polypeptide which has RANKL binding activity. The modified polynucleotide can encode any of the variants or fragments discussed above. Degenerate substitutions can be made and/or substitutions can be made which would result in a conservative amino acid substitution when the modified sequence is translated, for example as shown in the Table above.

A nucleotide sequence which is capable of selectively hybridizing to the complement of the DNA coding sequence of SEQ ID NO: 1, 4, 8 or 12 will generally have at least 60%, at least 70%, at least 80%, at least 90%, at least 95%, at least 98% or at least 99% sequence identity to the coding sequence of SEQ ID NO: 1, 4, 8 or 12 over a region of at least 20, preferably at least 30, for instance at least 40, at least 60, more preferably at least 100 contiguous nucleotides or most preferably over the full length of SEQ ID NO: 1, 4, 8 or 12 or the length of SEQ ID NO: 1, 4, 8 or 12 encoding a polypeptide having the sequence shown in SEQ ID NO: 2, 5, 9 or 13. Sequence identity can be determined by any suitable method, for example as described above.

Any combination of the above mentioned degrees of sequence identity and minimum sizes can be used to define polynucleotides of the invention, with the more stringent combinations (i.e. higher sequence identity over longer lengths) being preferred. Thus, for example a polynucleotide which has at least 90% sequence identity over 20, preferably over 30 nucleotides forms one aspect of the invention, as does a polynucleotide which has at least 95% sequence identity over 40 nucleotides.

Polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Fragments can be longer than 150 nucleotides in length, for example up to 200, 300, 400, 500, 600, 700, 800, 900 or 1000 nucleotides in length, or even up to a few nucleotides, such as five, ten or fifteen nucleotides, short of the coding sequence of SEQ ID NO: 1, 4, 8 or 12.

Polynucleotides for use in the invention can be produced recombinantly, synthetically, or by any means available to those of skill in the art. They can also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the TSG-6 gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the TSG-6 gene sequence described herein. Although in general the techniques mentioned herein are well known in the art, reference may be made in particular to Sambrook et al., 2001, Molecular Cloning: a laboratory manual, 3$^{rd}$ edition, Cold Harbour Laboratory Press.

TSG-6 polynucleotides as described herein have utility in production of the polypeptides for use in the present invention, which may take place in vitro, in vivo or ex vivo. The polynucleotides can be used as therapeutic agents in their own right or can be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention can be made by introducing a TSG-6 polynucleotide into a replicable vector, introducing the vector into a compatible host cell and growing the host cell under conditions which bring about replication of the vector.

Preferably the vector is an expression vector comprising a nucleic acid sequence that encodes a TSG-6 polypeptide. Such expression vectors are routinely constructed in the art of molecular biology and may for example involve the use of plasmid DNA and appropriate initiators, promoters, enhancers and other elements, such as for example polydenylation signals, which may be necessary and which are positioned in the correct orientation in order to allow for protein expression. Other suitable vectors would be apparent to persons skilled in the art. By way of further example in this regard we refer to Sambrook et al., 2001, Molecular Cloning: a laboratory manual, 3$^{rd}$ edition, Cold Harbour Laboratory Press.

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors can be for example, plasmid, virus or phage vectors provided with a origin of replication, optionally a promoter for the expression of the said polynucleotide and optionally a regulator of the promoter. The vector is typically adapted to be used in vivo.

Promoters and other expression regulation signals can be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector can further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

OPG Polypeptides

In a preferred embodiment of the invention, an OPG polypeptide is administered in combination with TSG-6 to treat or prevent a disease or condition associated with bone resorption by osteoclasts. The OPG polypeptide is preferably human OPG, or a variant or fragment of human OPG which retains RANKL binding activity. The OPG polypeptide has the ability to inhibit bone resorption by osteoclasts. The variant can be an OPG polypeptide from another organism, such as a primate, a mouse or a rat.

The OPG polypeptide preferably comprises:

(a) the amino acid sequence of SEQ ID NO: 15;

(b) a variant thereof having at least 50% identity to the amino acid sequence of SEQ ID NO: 15 and having receptor activator of RANKL binding activity; or (d) a fragment of either (a) or (b) having RANKL binding activity.

Preferably, the OPG polypeptide comprises, or consists of, the sequence of SEQ ID NO: 15.

Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 15 are considered variants of the OPG protein. Such variants include allelic variants and the deletion, modification or addition of single amino acids or groups of amino acids within the protein sequence, as long as the peptide maintains the basic functionality of OPG. The identity of variants of SEQ ID NO: 15 can be measured over various regions of SEQ ID NO: 15 as discussed above for TSG-6. The variant sequences typically differ from SEQ ID NO: 15 by one or more mutations as discussed above for TSG-6.

The fragment of the OPG polypeptide used in the invention retains the function of OPG. The fragment polypeptides therefore inhibit bone resorption by osteoclasts. The fragment polypeptides bind to RANKL.

The binding activity of the fragment polypeptides can be modified as discussed above for TSG-6.

The fragment of the OPG polypeptide used in the invention is typically at least 10 amino acids in length as discussed above for TSG-6.

The OPG polypeptides used in the invention may be chemically modified as discussed above for TSG-6.

The RANKL binding activity and the osteoclast inhibitory activity of the OPG polypeptide can be determined as discussed above for TSG-6.

OPG polypeptides for use in the invention may be in a substantially isolated form as discussed above for TSG-6. They may be natural polypeptides or be made synthetically or by recombinant means as discussed above for TSG-6.

The amino acid sequence of OPG polypeptides for use in the invention may be modified as discussed above for TSG-6.

OPG Polynucleotides

In a preferred embodiment of the invention, a polynucleotide encoding an OPG polypeptide, variant or fragment is administered in combination with TSG-6 to treat or prevent a disease or condition associated with bone resorption by osteoclasts. In particular the polynucleotide preferably comprises or consists of: (a) the coding sequence of SEQ ID NO: 14; (b) a sequence which is degenerate as a result of the genetic code to the sequence as defined in (a); (c) a sequence having at least 60% identity to a sequence as defined in (a) or (b) and which encodes a polypeptide having RANKL binding activity; or (d) a fragment of any one of the sequences as defined in (a), (b) or (c) which encodes a polypeptide having RANKL binding activity. The polynucleotide preferably comprises or consists of: (a) the coding sequence of SEQ ID NO: 14; (b) a sequence which is degenerate as a result of the genetic code to the sequence as defined in (a); (c) a sequence having at least 60% identity to a sequence as defined in (a) or (b) and which encodes a polypeptide having the ability to inhibit bone resorption by osteoclasts; or (d) a fragment of any one of the sequences as defined in (a), (b) or (c) which encodes a polypeptide having the ability to inhibit bone resorption by osteoclasts.

Typically the OPG polynucleotide is DNA. However, the polynucleotide may be a RNA polynucleotide. The polynucleotide may be single or double stranded, and may include within it synthetic or modified nucleotides.

An OPG polynucleotide can typically hybridize to the coding sequence or the complement of the coding sequence of SEQ ID NO: 14 as discussed above for TSG-6. The coding sequence of SEQ ID NO: 14 can be modified as discussed above for TSG-6.

A nucleotide sequence which is capable of selectively hybridizing to the complement of the DNA coding sequence of SEQ ID NO: 14 will generally have at least 60% identity to the coding sequence of SEQ ID NO: 14 over a region of at least 20 contiguous nucleotides or most preferably over the full length of SEQ ID NO: 14 or the length of SEQ ID NO: 14 encoding a polypeptide having the sequence shown in SEQ ID NO: 15 as discussed above for TSG-6.

Polynucleotide fragments will preferably be at least 10 nucleotides in length as discussed above for TSG-6.

OPG polynucleotides for use in the invention can be produced by any means discussed above for TSG-6. They can also be used to produce OPD polypeptides as discussed above for TSG-6.

OPG Mimetics

In a preferred embodiment of the invention, an OPG mimetic is administered in combination with TSG-6 to treat or prevent a disease or condition associated with bone resorption by osteoclasts. An OPG mimetic is a factor that inhibits bone resorption by osteoclasts by binding to and inhibiting RANKL.

The OPG mimetic can be a polypeptide, such as an antibody. The OPG mimetic is preferably AMG-162, which is Amgen's monoclonal antibody that binds to and inhbits RANKL. Alternatively, the OPG mimetic can be a polynucleotide which encodes a polypeptide that inhibits bone resorption by osteoclasts by binding to and inhibiting RANKL.

Diseases and Conditions

In accordance with the invention, the TSG-6 polypeptide, or polynucleotide, is used to treat or prevent diseases or conditions associated with bone resorption by osteoclasts. Bone resorption by osteoclasts is the breakdown of bone matrix and mineral by osteoclasts cells. A disease or condition associated with bone resorption by osteoclasts is a disease or condition in which the rate of bone resorption by osteoclasts is abnormal. A disease or condition associated with bone resorption by osteoclasts is a disease or condition in which osteoclasts resorb (break down) bone at a greater rate than the rate of bone resorption (break down) observed in comparable subjects in the absence of the disease or condition. The disease or condition involves an increase in the rate of bone resorption by osteoclasts.

The disease or condition can involve a rate of bone resorption that is greater than the rate of bone formation in the same subject. The disease or condition can therefore involve a net bone loss. Alternatively, the disease or condition can involve a rate of bone resorption that is the same as or less than the rate of bone formation in the same subject. The disease or condition can involve no net bone loss. The disease or condition can involve net bone gain. The disease or condition can involve a slower rate of net bone gain compared with the rate of net bone gain observed in comparable subjects without the disease or condition.

The disease or condition is preferably osteoarthritis, osteoporosis, bone cancer, a bone lesion associated with metastatic cancer, Paget's disease, Gorham Stout disease, primary hyperparathyroidism, periodontal disease, a bone fracture and/or aseptic loosening of joint replacements. The bone cancer can be Ewing sarcoma, multiple myeloma, osteosarcoma (giant tumour of the bone) and/or osteoclastoma. The metastatic cancer that results in a bone lesion can be breast cancer, prostate cancer, kidney cancer, lung cancer and/or adult T-cell leukemia.

The subject is typically a mammalian subject, such as a mouse, rat or primate (e.g. a marmoset or monkey). The subject can be human or a non-human animal. Where the subject is a laboratory animal such as a mouse, rat or primate, the animal can be treated to induce a disease or condition associated with bone resorption by osteoclasts. The following Table summarizes whether an animal model for a disease or condition associated with bone resorption by osteoclasts exists or how a disease or condition associated with bone resorption by osteoclasts can be induced in an animal model.

| Disease or condition | Model/Induction |
| --- | --- |
| Osteoarthritis | Partial lateral meniscectomy in the knees of rabbits/mice or STR/ort mouse model |
| Osteoporosis | Ovariectomization of rodents such as rats |
| Ewing sarcoma | Injection of primary tumor cells into immune-deficient mice e.g. NOD or SCID |

| Disease or condition | Model/Induction |
| --- | --- |
| Multiple myeloma | 5TMM mouse model |
| Osteosarcoma | Injection of TE-85 osteosarcoma cell line into tibia of athymic mice |
| Breast cancer | Implantation of mouse cancer cells 4T1/luc at the mammary fat pad, or injection of MDA-MB-231 human breast cancer cell line into nude mice |
| Kidney | Injection of RBM1 renal cancer cell line into nude mice |
| Lung | Injection of POS-1 cell line into C3H/He mice |
| Prostate | Injection of 22Rv1 prostate cancer cells into SCID mice |
| Adult T-cell leukaemia | HTLV-1 Tax transgenic mouse model |
| Primary hyperparathyroidism | PTH-targeted over-expression of cyclin D1 in transgenic mice |
| Periodontal diseases | Naturally occurring beagle dog model of periodontitis |
| Bone fracture | Wistar rat model of femoral fracture |
| Aseptic loosening of joint replacements | Weight-bearing rat pin model |

Therapy and Prophylaxis

The present invention provides the use of TSG-6 polypeptides and polynucleotides to treat or prevent a disease or condition associated with bone resorption by osteoclasts. Treatment can be therapeutic or prophylactic.

The TSG-6 polypeptide or polynucleotide can be administered to an individual in order to prevent the onset of one or more symptoms of the disease or condition. In this embodiment, the subject can be asymptomatic. The subject can have a genetic predisposition to the disease. A prophylactically effective amount of the polypeptide or polynucleotide is administered to such an individual. A prophylactically effective amount is an amount which prevents the onset of one or more symptoms of a disease or condition.

A therapeutically effective amount of the TSG-6 polypeptide or polynucleotide is an amount effective to ameliorate one or more symptoms of a disease or condition. Preferably, the individual to be treated is human.

The TSG-6 polypeptide or polynucleotide can be administered to the subject by any suitable means. The polypeptide or polynucleotide can be administered by enteral or parenteral routes such as via oral, buccal, anal, pulmonary, intravenous, intra-arterial, intramuscular, intraperitoneal, intraarticular, topical or other appropriate administration routes.

The TSG-6 polypeptide or polynucleotide may be administered to the subject in such a way as to target therapy to a particular site. For example, the TSG-6 polypeptide may be injected locally onto the surface of bone. The TSG-6 polypeptide may be conjugated with reagents that bind bone or osteoclasts specifically. For TSG-6 polynucleotides, expression vectors encoding the TSG-6 polypeptide may be used to direct expression of TSG-6 to a particular tissue, for example by using tissue-specific promoters or RNAi.

The formulation of any of the polypeptides and polynucleotides mentioned herein will depend upon factors such as the nature of the polypeptide or polynucleotide and the condition to be treated. The polypeptide or polynucleotide may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The polypeptide or polynucleotide may also be administered as suppositories. A physician will be able to determine the required route of administration for each particular patient.

Typically the polypeptide or polynucleotide is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically effective amount of polypeptide or polynucleotide is administered. The dose may be determined according to various parameters, especially according to the polypeptide or polynucleotide used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The TSG-6 nucleotide sequences described above and expression vectors containing such sequences can also be used as pharmaceutical formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

The present invention also provides a method of treating, ex vivo, blood taken from a patient suffering from a disease or condition associated with bone resorption by osteoclasts comprising contacting the blood with a TSG-6 polypeptide. TSG-6 may thus be used for extracorporeal treatment of blood. The TSG-6 may be used to treat one or more components of blood, such as plasma or serum. The ex vivo method described herein may be practised on blood that has already been removed from the body of a patient. The blood or blood product may optionally be returned to the patient after being contacted with a TSG-6 polypeptide.

Combination Therapy

The TSG-6 polypeptide or polynucleotide can be administered alone or in combination with other pharmaceutically active agents. In one embodiment, the TSG-6 polypeptide or polynucleotide is not administered in combination with long petraxin 3 (PTX3). In the same embodiment, the medicament manufactured in accordance with the invention does not comprise PTX3.

In a preferred embodiment, the method further comprises administering to the subject a therapeutically or prophylactically effective amount of an OPG polypeptide, a polynucleotide encoding an OPG polypeptide or an OPG mimetic. In the same embodiment, the medicament is administered in combination with a therapeutically or prophylactically effective amount of an OPG polypeptide, a polynucleotide encoding an OPG polypeptide or an OPG mimetic.

The TSG-6 and OPG act synergistically. In other words, administering TSG-6 and OPG in combination has a greater effect on inhibiting bone resorption by osteoclasts than the sum of the effect of each alone.

A therapeutically effective amount of the OPG polypeptide, polynucleotide or an OPG mimetic is an amount effective to ameliorate one or more symptoms of a disease or condition. A prophylactically effective amount is an amount which prevents the onset of one or more symptoms of a disease or condition.

The TSG-6 and OPG can be administered simultaneously, separately or sequentially. If administered simultaneously, the TSG-6 and OPG can be present in the same medicament or different medicaments. If administered separately or sequentially, the TSG-6 and OPG can be administered in any order.

Typically, a TSG-6 polypeptide and an OPG polypeptide are administered together or a TSG-6 polynucleotide and an OPG polynucleotide are administered together. However, in some embodiments, the TSG-6 may be a polypeptide, while the OPG is a polynucleotide and vice versa.

The OPG polypeptide, the OPG polynucleotide or the OPG mimetic can be administered to the subject by any means, in any formulation and at any dose discussed above for TSG-6.

The following Examples illustrate the invention:

EXAMPLES

The following studies show that TSG-6 is a novel inhibitor of bone resorption.

Example 1

Inhibition of Osteoclasts by TSG-6

Figure 2:
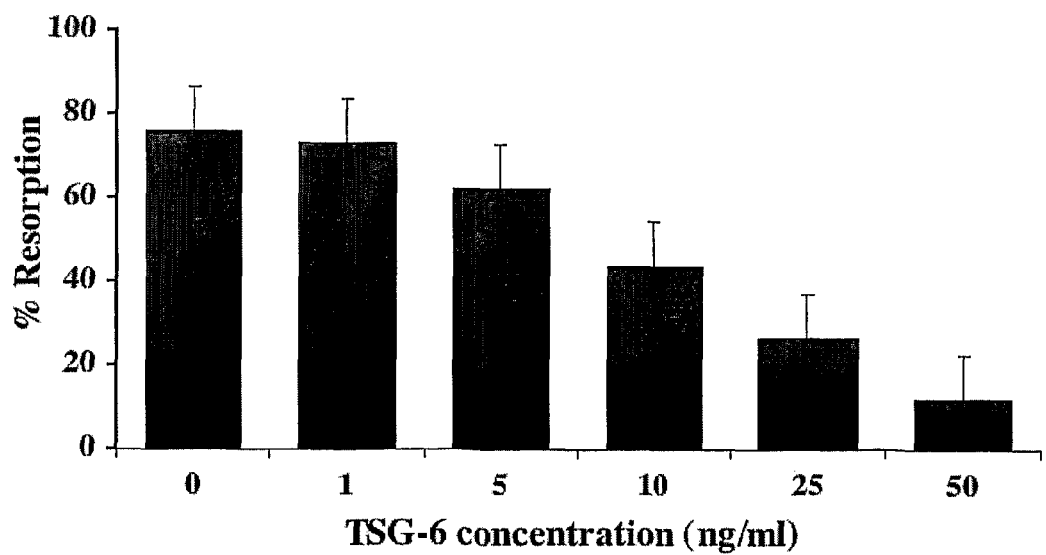
FIG. 2 shows the inhibitory effect of TSG-6 on lacunar resorption over a range of TSG-6 concentrations. Data (n=8 dentine slices) are expressed as mean values±S.E. of 2 independent experiments, of 4 replicates each.

The Q144 allotype of the full-length human TSG-6 protein (as shown in SEQ ID NO: 1) was expressed in *Drosophila* S2 cells as described in Nentwich et al. (2002) *J. Biol. Chem.* 277, 15354-15362. The effect of this recombinant protein on the differentiation of osteoclasts in vitro was determined. Human monocytes differentiated into osteoclasts and developed a bone-resorbing phenotype over a period of 21 days. Osteoclast activity was measured by determining the extent of lacunar resorption on dentine slices. Human monocytes were cultured in the presence of sRANKL (soluble receptor activator of NFκB ligand; 30 ng/ml) and/or M-CSF (25 ng/ml) and bone resorptive activity was measured in the presence or absence of recombinant TSG-6. The addition of TSG-6 to this culture system mediated a substantial reduction in dentine erosion (FIG. 1) and this effect is dose-dependent (FIG. 2). TSG-6 therefore inhibits bone resorption by osteoclasts.

Example 2

Osteoclast Activity in TSG-6 Knockout Mice

Figure 3:
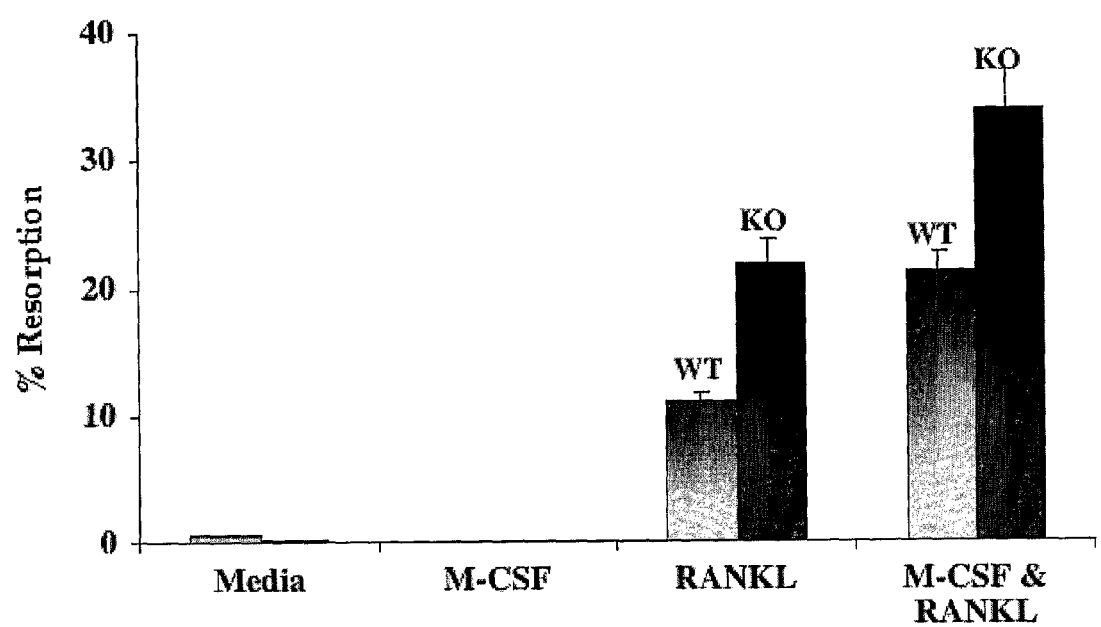
FIG. 3 shows a comparison of the bone resorptive activities of osteoclasts derived from bone marrow of wild-type (WT, left hand side bars) and TSG-1$^{-/-}$ mice (KO, right hand side bars). Data (n=4 dentine slices) are expressed as mean values±S.E. of 2 independent experiments, of 4 replicates.

The same experiment as in Example 1 was also carried out using osteoclast precursors from the long bones of TSG-6$^{-/-}$ mice. When cultured in the presence of sRANKL or M-CSF and sRANKL, the osteoclasts displayed markedly increased lacunar resorption in vitro as compared to cells from wild-type control animals (FIG. 3). These results are consistent with the more severe symptoms (e.g. bone erosion) seen in TSG-6-deficient animals following induction of PGIA. These studies indicate that TSG-6 is an important, novel inhibitor of osteoclastogenesis and/or osteoclast activation.

Example 3

TSG-6 Binding to RANKL

RANKL and its receptor RANK are key regulators of bone remodelling and have been specifically implicated in the bone loss that occurs in RA. RANKL is a membrane bound TNF-superfamily ligand that is produced by osteoblasts and other stromal cells, while RANK, a transmembrane signalling molecule, is expressed on the surfaces of mononuclear osteoclast precursors. RANKL binds to RANK, in response to calciotropic factors such as $PGE_2$, IL-1 and TNF, where this interaction not only induces osteoclast differentiation, but also stimulates the bone resorbing activity of mature osteoclasts (reviewed in Tanake et al. (2005) *Immunol. Rev.* 208, 30-49). Indeed, RANKL (in combination with M-CSF) is the major factor that regulates osteoclast differentiation (Quinn et al. (1998) *Endocrinology* 139, 4424-4427).

At present, osteoprotegerin (OPG), a soluble decoy receptor to RANKL, is the only known inhibitor of the RANKL/RANK interaction that can effectively inhibit osteoclast maturation and activation in vitro (Simonet et al. (1997) *Cell* 89, 309-319), and a mimic of OPG activity (AMG 162) is currently in clinical trials for the treatment of osteoporosis.

RANKL is also expressed on the surfaces of synovial effector T cells from RA patients and studies on rats with AIA (which has many features in common with human RA) showed RANKL to be the key mediator of joint damage and bone erosion due to osteoclast accumulation, where treatment with OPG provided protection against these effects (Kong et al. (1999) *Nature* 402, 304-309).

Given the effects of TSG-6 on bone resorption described in Examples 1 and 2 above, the interaction of TSG-6 directly with RANKL was investigated. Recombinant full-length TSG-6 was expressed as described in Example 1. The isolated Link module domain (Link_TSG-6; SEQ ID NO: 9) was expressed in *E. coli* as described in Day et al. (1996) *Protein Express. Purif.* 8, 1-16. The CUB_C domain (CUB_C_TSG6; SEQ ID NO: 13) was expressed in *E. coli* (D J Mahoney and A J Day, unpublished). Full-length TSG-6, Link_TSG6 or CUB_C_TSG6 were coated onto microtitre plates at a range of concentrations and the binding of sRANKL (5 pmol/well) was determined using a RANKL-specific antibody.

Figure 4:
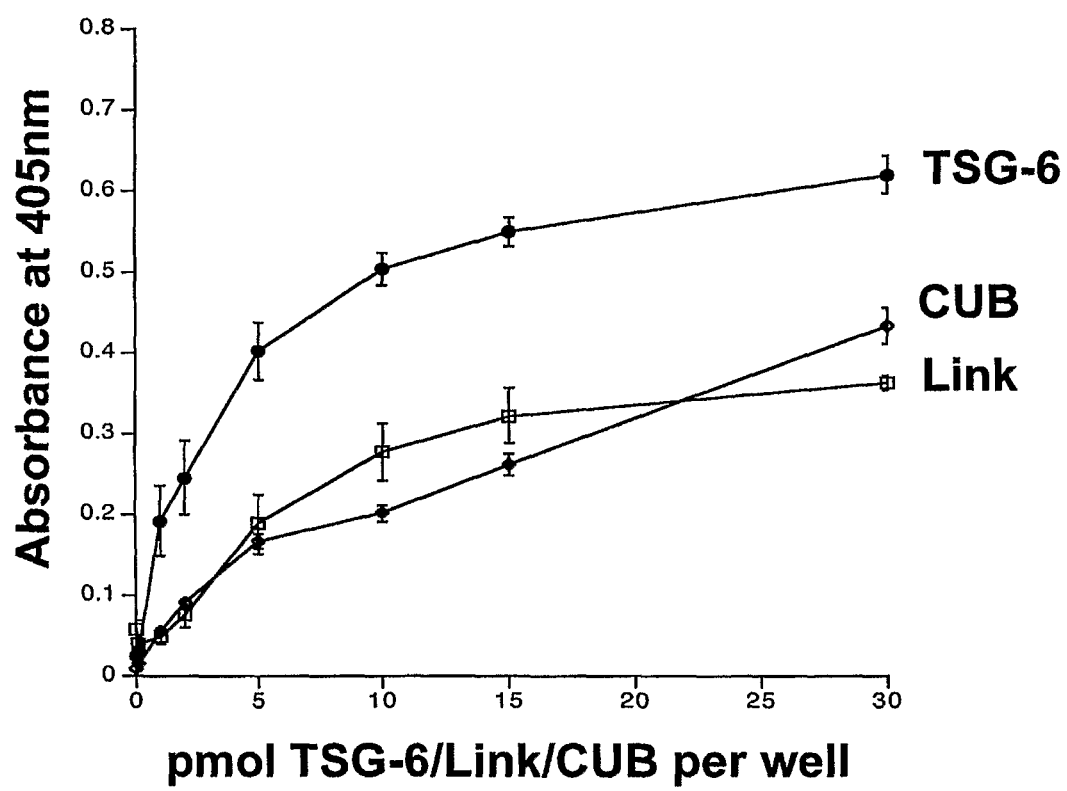
FIG. 4 shows the interaction of TSG-6 with sRANKL. Full-length TSG-6, Link_TSG6 or CUB_C_TSG6 were coated onto microtitre plates at a range of concentrations and the binding of sRANKL (5 pmol/well) was determined using a RANKL-specific antibody. All data are plotted as mean absorbance (405 nm) values (n=8)±S.E.

Results of plate-binding assays indicate that full-length TSG-6, its isolated Link module domain (Link_TSG6; SEQ ID NO: 9) and isolated CUB_C domain (CUB_C_TSG6; SEQ ID NO: 13) all bind to sRANKL but that the full-length TSG-6 has a higher binding affinity than the isolated domains (FIG. 4). This data suggests that TSG-6 might inhibit RANKL-induced osteoclastogenesis/osteoclast activation by its direct binding to RANKL, potentially in a similar manner to OPG.

Example 4

Synergy Between TSG-6 and OPG

Our data (not shown) indicates that TSG-6 in combination with OPG (a known inhibitor of RANKL) has a synergistic effect on the inhibition of osteoclast formation as determined by the number of tartrate-resistant acid phosphatase (TRAP+) multinucleated osteoclasts formed in culture (i.e., there is more inhibition of osteoclast formation in the presence of both TSG-6 and OPG compared to experiments where the individual proteins are present). One possible mechanism that could explain the synergistic action of TSG-6 and OPG is that both these proteins can bind simultaneously to RANKL forming a stable ternary complex.

Example 5

Link and CUB_C_Domains of TSG-6 Inhibit Osteoclastogenesis

Moreover, our data (not shown) also shows that the isolated Link and CUB_C domains are inhibitors of osteoclastogenesis, albeit with less activity than the full-length protein. This indicates that these fragments of TSG-6 could be used as the basis for design of inhibitors of bone resorption.

Example 6

Levels of TSG-6 and OPG in Synovial Fluid

Figure 5:
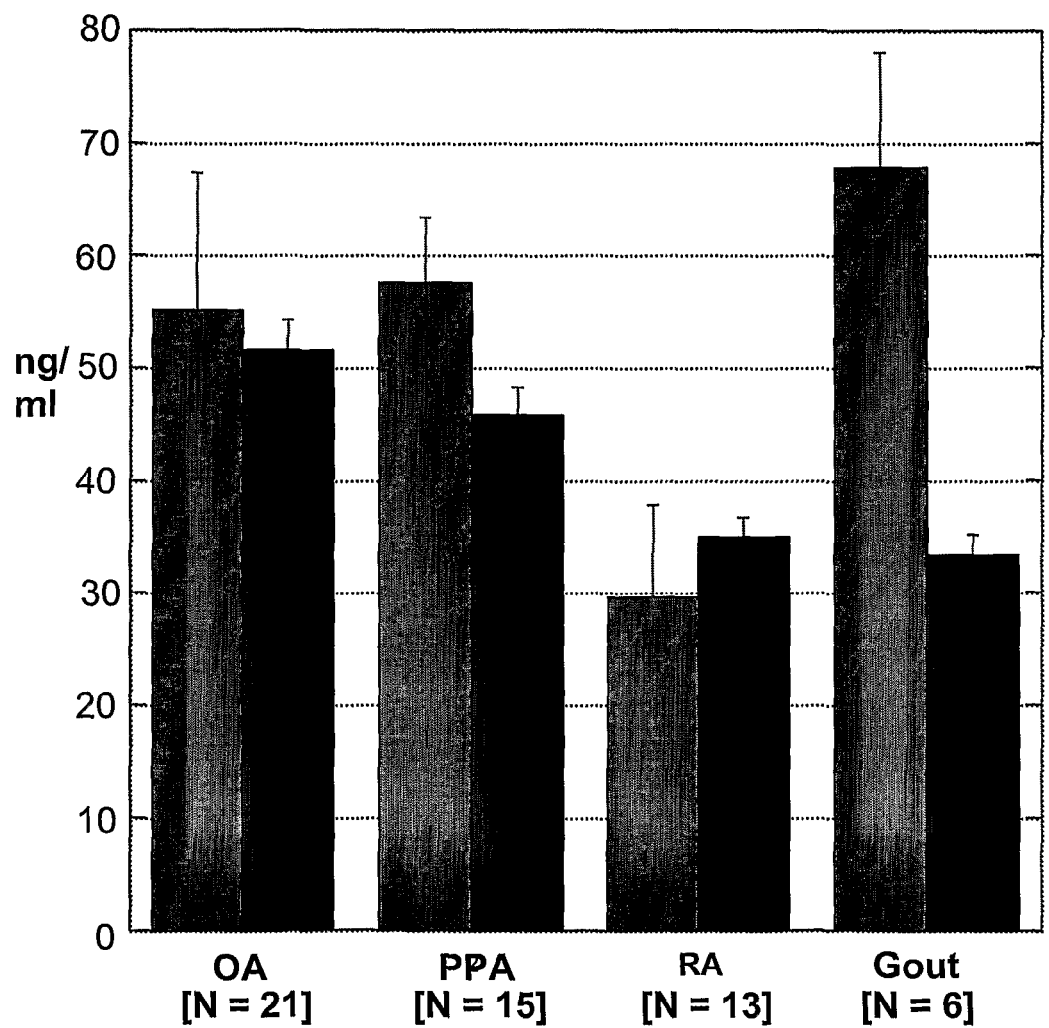
FIG. 5 shows quantification of TSG-6 and OPG in the synovial fluid from patients with various bone disorders. Protein levels in various bone disorders were determined using "in-house designed" ELISA assays. The levels of TSG-6 are shown in the lighter bars on the left hand side. The levels of OPG are shown in the darker bars on the right hand side. This Figure indicates variation in the levels of TSG-6 and OPG depending on the severity and stage of the bone diseases osteoarthritis (OA), pyrophosphate arthropathy (PPA), rheumatoid arthritis (RA) and gout. Each sample was assessed in triplicate and the number of synovial fluid samples for each condition is given (N number). The values are expressed as the mean±standard error of the mean for each group.
Figure 6:
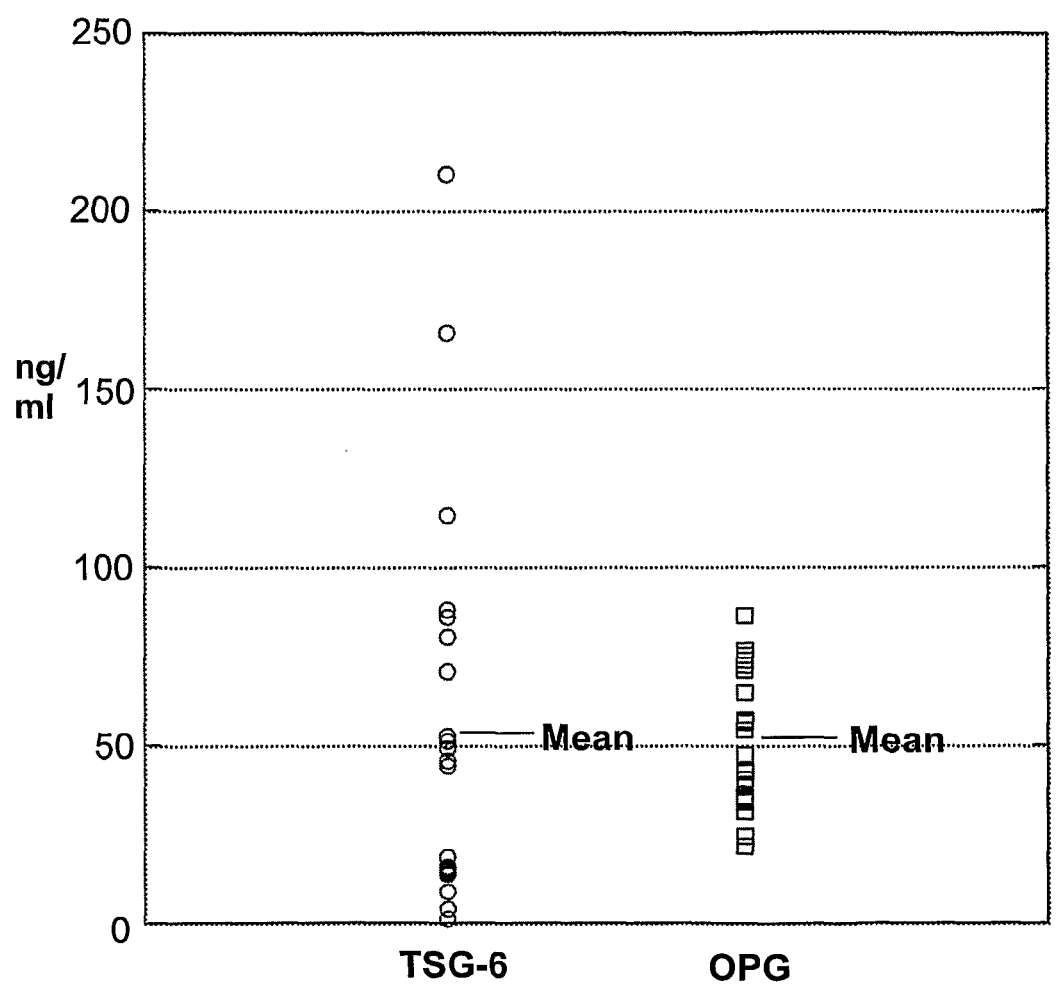
FIG. 6 shows a comparison between TSG-6 and OPG levels in the synovial fluid samples of osteoarthritis (OA) patients (n=20). This data demonstrates that variability in levels of TSG-6, as compared to OPG levels, could contribute to the extent and severity of disease.

We have measured high levels of TSG-6 (ranging from 0-200 ng/ml) in synovial fluid of patients with various bone disorders [e.g. osteoarthritis (OA), rheumatoid arthritis (RA), gout & pyrophosphate arthropathy (PPA); see FIG. 5). ELISA analyses of TSG-6 and OPG levels in OA synovial samples have shown that there is more patient-to-patient variation in the levels of TSG-6 protein compared to OPG (see FIG. 6). This suggests that absence/low levels of TSG-6 could contribute to the extent and severity of osteolytic diseases.

---

The invention claimed is:

1. A method of treating osteoporosis in a subject in need thereof, the method comprising administering to the subject a therapeutically effective amount of a TSG-6 polypeptide, wherein the TSG-6 polypeptide is not administered in combination with PTX3;
    wherein the TSG-6 polypeptide comprises:
    (i) the amino acid sequence of SEQ ID NO: 2, 3, 5, 6, 7, 9, 10, 11 or 13, or
    (ii) an amino acid sequence having at least 95% identity to the amino acid sequence of SEQ ID NO: 2, 3, 5, 6, 7, 9, 10, 11 or 13.

2. The method according to claim 1, wherein said TSG-6 polypeptide has RANKL binding activity.

3. The method according to claim 2, wherein said polypeptide consists of the sequence shown in SEQ ID NO:2 or 5.

4. The method according to claim 1, wherein said TSG-6 polypeptide is administered simultaneously, separately, or sequentially with a therapeutically effective amount of an OPG polypeptide, wherein the OPG polypeptide comprises:
    (i) the amino acid sequence set fourth in SEQ ID NO:15, or
    (ii) an amino acid sequence having least 90% identity to the amino acid sequence set forth SEQ ID NO:15 and having RANKL binding activity.

5. The method according to claim 1, wherein said TSG-6 polypeptide is administered in combination with a therapeutically effective amount of an OPG polypeptide, wherein the OPG polypeptide comprises:
    (i) the amino acid sequence set forth in SEQ ID NO:15, or
    (ii) an amino acid sequence having at least 90% identity to the amino sequence set forth in SEQ ID NO:15 and having RANKL binding activity.

* * * * *